US008814939B2

(12) United States Patent
Ullrich, Jr. et al.

(10) Patent No.: US 8,814,939 B2
(45) Date of Patent: Aug. 26, 2014

(54) IMPLANTS HAVING THREE DISTINCT SURFACES

(75) Inventors: Peter F. Ullrich, Jr., Neenah, WI (US); Chad J. Patterson, Port Washington, WI (US); Jennifer M. Schneider, Germantown, WI (US)

(73) Assignee: Titan Spine, LLC, Mequon, WI (US)

( * ) Notice: Subject to any disclaimer, the term of this patent is extended or adjusted under 35 U.S.C. 154(b) by 0 days.

(21) Appl. No.: 13/557,727

(22) Filed: Jul. 25, 2012

(65) Prior Publication Data

US 2012/0316650 A1    Dec. 13, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)
(52) U.S. Cl.
USPC .................................. 623/17.16; 623/17.11
(58) Field of Classification Search
USPC ............................................ 623/17.11–17.16
See application file for complete search history.

(56) References Cited

U.S. PATENT DOCUMENTS

| | | |
|---|---|---|
| 4,314,876 A | 2/1982 | Kremer et al. |
| 4,834,757 A | 5/1989 | Brantigan |
| 4,904,261 A | 2/1990 | Dove et al. |
| 5,015,247 A | 5/1991 | Michelson |
| 5,071,437 A | 12/1991 | Steffee |
| 5,258,098 A | 11/1993 | Wagner et al. |
| 5,306,308 A | 4/1994 | Gross et al. |
| 5,306,309 A | 4/1994 | Wagner et al. |
| 5,425,772 A | 6/1995 | Brantigan |
| 5,443,514 A | 8/1995 | Steffee |
| 5,456,723 A | 10/1995 | Steinemann et al. |
| 5,507,815 A | 4/1996 | Wagner et al. |

(Continued)

FOREIGN PATENT DOCUMENTS

| | | |
|---|---|---|
| EP | 0599419 | 6/1994 |
| EP | 0916323 | 5/1999 |

(Continued)

OTHER PUBLICATIONS

Astra Tech Dental, "Nanolevel topographic modifications on the OsseoSpeed surface", http://shop.dentsplyimplants.us, Mar. 8, 2001.

(Continued)

*Primary Examiner* — Eduardo C. Robert
*Assistant Examiner* — Julianna N Harvey
(74) *Attorney, Agent, or Firm* — Stradley Ronon Stevens & Young, LLP

(57) ABSTRACT

An interbody spinal implant having at least three distinct surfaces including (1) at least one integration surface having a roughened surface topography including macro features, micro features, and nano features, without sharp teeth that risk damage to bone structures; (2) at least one graft contact surface having a coarse surface topography including micro features and nano features; and (3) at least one soft tissue surface having a substantially smooth surface including nano features. Also disclosed are processes of fabricating the different surface topographies, which may include separate macro processing, micro processing, and nano processing steps.

22 Claims, 16 Drawing Sheets

(56) References Cited

U.S. PATENT DOCUMENTS

| | | | |
|---|---|---|---|
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,755,798 A | 5/1998 | Papavero et al. | |
| 5,766,252 A | 6/1998 | Henry et al. | |
| 5,776,199 A | 7/1998 | Michelson | |
| 5,860,973 A | 1/1999 | Michelson | |
| 5,863,201 A | 1/1999 | Lazzara et al. | |
| 5,865,845 A * | 2/1999 | Thalgott | 623/17.16 |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlaepfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,143,032 A | 11/2000 | Schafer et al. | |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,425,920 B1 | 7/2002 | Hamada | |
| 6,432,140 B1 | 8/2002 | Lin | |
| 6,436,102 B1 | 8/2002 | Ralph et al. | |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,412 B2 | 3/2006 | Ferreira et al. | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Lie et al. | |
| 7,128,760 B2 | 10/2006 | Michelson | |
| 7,137,997 B2 | 11/2006 | Paul | |
| 7,141,068 B2 | 11/2006 | Ross et al. | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,244,275 B2 | 7/2007 | Michelson | |
| 7,250,060 B2 | 7/2007 | Trieu | |
| 7,255,698 B2 | 8/2007 | Michelson | |
| 7,288,093 B2 | 10/2007 | Michelson | |
| 7,311,734 B2 | 12/2007 | Van Hoeck et al. | |
| D564,095 S | 3/2008 | Blain | |
| 7,347,873 B2 | 3/2008 | Paul et al. | |
| D566,276 S | 4/2008 | Blain | |
| 7,368,065 B2 | 5/2008 | Yang et al. | |
| 7,410,501 B2 | 8/2008 | Michelson | |
| 7,501,073 B2 | 3/2009 | Wen et al. | |
| 7,503,933 B2 | 3/2009 | Michelson | |
| 7,517,363 B2 | 4/2009 | Rogers et al. | |
| D599,019 S | 8/2009 | Pimenta et al. | |
| 7,569,074 B2 | 8/2009 | Eisermann et al. | |
| 7,608,107 B2 | 10/2009 | Michelson | |
| 7,615,078 B2 | 11/2009 | White et al. | |
| 7,655,042 B2 | 2/2010 | Foley et al. | |
| 7,662,186 B2 | 2/2010 | Bagga et al. | |
| 7,662,190 B2 | 2/2010 | Steinemann et al. | |
| 7,744,612 B2 | 6/2010 | Blain | |
| 7,846,183 B2 | 12/2010 | Blain | |
| 7,901,462 B2 | 3/2011 | Yang et al. | |
| 7,998,172 B2 | 8/2011 | Blain | |
| 8,062,304 B2 | 11/2011 | Blain et al. | |
| 8,100,955 B2 | 1/2012 | Blain et al. | |
| 8,142,355 B2 | 3/2012 | Blain et al. | |
| 8,172,854 B2 | 5/2012 | Blain et al. | |
| 8,262,737 B2 | 9/2012 | Bagga et al. | |
| 2001/0014826 A1 | 8/2001 | Biedermann et al. | |
| 2001/0016777 A1 | 8/2001 | Biscup | |
| 2001/0039454 A1 | 11/2001 | Ricci et al. | |
| 2001/0047208 A1 | 11/2001 | Michelson | |
| 2002/0049497 A1 | 4/2002 | Mason | |
| 2002/0087212 A1 | 7/2002 | James et al. | |
| 2002/0099443 A1 | 7/2002 | Messerli et al. | |
| 2002/0128716 A1 | 9/2002 | Cohen et al. | |
| 2002/0138142 A1 | 9/2002 | Castro et al. | |
| 2002/0156529 A1 * | 10/2002 | Li et al. | 623/17.11 |
| 2002/0161443 A1 | 10/2002 | Michelson | |
| 2002/0173854 A1 | 11/2002 | Amrich | |
| 2002/0188294 A1 | 12/2002 | Couture et al. | |
| 2003/0014116 A1 | 1/2003 | Ralph et al. | |
| 2003/0083668 A1 | 5/2003 | Rogers et al. | |
| 2003/0105527 A1 | 6/2003 | Bresina | |
| 2003/0109928 A1 | 6/2003 | Pasquet et al. | |
| 2003/0125739 A1 | 7/2003 | Bagga et al. | |
| 2003/0153975 A1 | 8/2003 | Byrd, III et al. | |
| 2003/0176925 A1 | 9/2003 | Paponneau | |
| 2003/0181980 A1 | 9/2003 | Berry et al. | |
| 2003/0181981 A1 | 9/2003 | Lemaire | |
| 2003/0187506 A1 | 10/2003 | Ross et al. | |
| 2003/0191531 A1 | 10/2003 | Berry et al. | |
| 2004/0073314 A1 * | 4/2004 | White et al. | 623/17.15 |
| 2004/0117019 A1 | 6/2004 | Trieu et al. | |
| 2004/0117020 A1 | 6/2004 | Frey et al. | |

(56) References Cited

U.S. PATENT DOCUMENTS

| | | |
|---|---|---|
| 2004/0122518 A1 | 6/2004 | Rhoda |
| 2004/0127993 A1 | 7/2004 | Kast et al. |
| 2004/0134886 A1 | 7/2004 | Wagner et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1 | 2/2005 | Webb et al. |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0119758 A1 | 6/2005 | Alexander et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1 | 9/2005 | Pope et al. |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1* | 1/2009 | White et al. ............... 623/17.11 |
| 2009/0014243 A1 | 1/2009 | Whigham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0076559 A1 | 3/2010 | Bagga et al. |
| 2010/0094426 A1 | 4/2010 | Grohowski, Jr. et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1 | 1/2011 | Ankem |
| 2011/0040301 A1 | 2/2011 | Blain et al. |
| 2011/0082503 A1 | 4/2011 | Blain |
| 2011/0190902 A1 | 8/2011 | Tong et al. |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ullrich, Jr. et al. |
| 2012/0239150 A1 | 9/2012 | Ullrich, Jr. et al. |
| 2012/0239151 A1 | 9/2012 | Ullrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

(56) References Cited

OTHER PUBLICATIONS

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011.

Supplementary Partial European Search Report issued Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

Wennerberg, A., et al., "Effects of titanium surface topography on bone integration: a systematic review", Clin. Oral Impl. Res., 20 (Suppl. 4), 2009, pp. 172-184.

Pending U.S. Appl. No. 13/286,813 of Chad J. Patterson, et al. filed Nov. 1, 2011.

Pending U.S. Appl. No. 13/826,304 of Peter F. Ullrich, Jr., et al. filed Mar. 14, 2013.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

\* cited by examiner

Ra = Average(1, 4, 6, 8, 5, 2, 1, 4, 1, 2, 1, 4, 7, 4, 1, 2, 5, 8, 2, 1, 4, 1, 1)

Ra = 3.26

Rpm = average(Rp1, Rp2, Rp3, ...)
Rvm = average(Rv1, Rv2, Rv3, ...)
RzDIN = Rtm = average(Rt1, Rt2, Rt3, ...)

IMPLANTS HAVING THREE DISTINCT SURFACES

CROSS REFERENCE TO RELATED APPLICATIONS

This application is a continuation-in-part of U.S. patent application Ser. No. 12/151,198, filed on May 5, 2008, now U.S. Pat. No. 8,262,737 which is a continuation-in-part of U.S. patent application Ser. No. 11/123,359, filed on May 6, 2005, and issued as U.S. Pat. No. 7,662,186. The contents of both prior applications are incorporated by reference into this document, in their entirety and for all purposes.

TECHNICAL FIELD

The present invention relates generally to interbody spinal implants and methods of making such implants and, more particularly, to spinal implants having at least three distinct surfaces.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

SUMMARY OF THE INVENTION

The present invention provides for interbody spinal implants having at least three distinct surfaces: (1) at least one integration surface; (2) at least one graft contact surface; and (3) at least one soft tissue surface. The integration surface includes macro, micro, and nano features having a fusion and biologically active surface geometry and frictionally engages preserved bone structures. The graft contact surface includes micro and nano features, which positively influence naturally occurring biological bone remodeling and fusion responses. The soft tissue surface includes a low friction surface with nano features (and optionally micro features) to avoid unintentional laceration or abrasion of delicate soft tissues (e.g., blood vessels, nerves, and muscles) the implant contacts during insertion, after insertion, or both. The soft tissue surface can also provide an anchoring point and signaling function to bone forming cells in order to positively influence the fusion and healing processes. Various implant body shapes are provided to allow for implantation through various access paths to the spine through a patient's body. The structures and surfaces are designed to work in concert to preserve endplate bone structures, provide for sufficient bioactivity in each respective location, and provide stability within the disc space and the graft containment axial column. In particular, the shapes and textures of the bioactive surfaces vary based on the implant insertion path, location within the disc space, and frictional characteristics of the surfaces.

In one embodiment, the present invention provides an implant comprising a body having a top surface, a bottom surface, opposing lateral sides, opposing anterior and posterior portions, a substantially hollow center, and a single vertical aperture; and optionally, at least one of a first integration plate affixed to the top surface of the body and a second integration plate affixed to the bottom surface of the body, wherein the first integration plate and the second integration plate each have a top surface, a bottom surface, opposing lateral sides, opposing anterior and posterior portions, and a single vertical aperture extending from the top surface to the bottom surface and aligning with the single vertical aperture of the body. The interbody spinal implant further comprises (a) at least one integration surface having a roughened surface topography including macro features, micro features, and nano features, without sharp teeth that risk damage to bone structures; (b) at least one graft contact surface having a coarse surface topography including micro features and nano features; and (c) at least one soft tissue surface having a substantially smooth surface including nano features and optionally, micro features.

The integration surface may include the top, bottom, or both surfaces of the implant. In the case of no integration plates, this would include the top, bottom, or both surfaces of the body of the implant. In the case of one integration plate affixed to the top of the body of the implant, this would include the top of the integration plate, the bottom of the body, or both surfaces. In the case of one integration plate affixed to the bottom of the body of the implant, this would include the top of the body, the top of the integration plate (i.e., the outer surface of the integration plate at the bottom of the implant), or both surfaces. In the case of two integration plates sandwiched around the body of the implant, this would include the top of the first integration plate, the top of the second integration plate, or both surfaces (i.e., the outer surfaces of both integration plates at the top and bottom of the implant).

The graft contact surface may include the interior surfaces of the implant. In other words, the graft contact surfaces may include any surfaces that may be in contact with bone growth inducing materials (once added to the inside of the implant). In particular, the surfaces typically in contact with bone growth inducing materials include one or more surfaces defined by the single vertical aperture, one or more surfaces defined by at least one transverse aperture, and one or more surfaces defined by one or more openings in the implant.

The soft tissue surface may include the exterior surfaces of the implant, except for the integration surface. In other words, other than the one or more integration surfaces, the soft tissue surfaces may include any outer surfaces which may contact bone or soft tissue during or after implantation. In particular, the soft tissue surface may include the opposing lateral sides of the body and the opposing anterior and posterior portions of the body. In the case of one integration plate, the soft tissue surface may additionally include the opposing lateral sides of the integration plate and the opposing anterior and posterior portions of the integration plate. In the case of two integration plates, the soft tissue surface may additionally include the opposing lateral sides of both integration plates and the opposing anterior and posterior portions of both integration plates. The soft tissue surface may also include any rounded edges on the interbody spinal implant including rounded edges on the body or either or both of the integration plates.

The implant body and/or the integration plate(s) may be fabricated from a metal. A preferred metal is titanium or a titanium alloy. The implant body may be fabricated from both a metal and a non-metallic material. In an exemplary embodiment, a composite implant may be formed with integration plates made of titanium combined with a body also made of titanium.

In another embodiment of the invention, a composite interbody spinal implant comprises a body having a top surface, a bottom surface, opposing lateral sides, opposing anterior and posterior portions, a substantially hollow center, a single vertical aperture, and at least one transverse aperture; a first integration plate affixed to the top surface of the body; and a second integration plate affixed to the bottom surface of the body. The first integration plate and the second integration plate each have a top surface comprising an integration surface, a bottom surface, opposing lateral sides, opposing anterior and posterior portions, and a single vertical aperture extending from the top surface to the bottom surface and aligning with the single vertical aperture of the body, defining a transverse rim. The top surface of the first integration plate and the top surface of the second integration plate may each have a roughened surface topography including macro features, micro features, and nano features, without sharp teeth that risk damage to bone structures, adapted to grip bone through friction generated when the implant is placed between two vertebrae and to inhibit migration of the implant. A surface defined by the single vertical aperture, a surface defined by the at least one transverse aperture, and a surface defined by an optional opening may each comprise a graft contact surface having a coarse surface topography including micro features and nano features. The opposing lateral sides of the body, the opposing anterior and posterior portions of the body, the opposing lateral sides of the first integration plate, the opposing anterior and posterior portions of the first integration plate, the opposing lateral sides of the second integration plate, the opposing anterior and posterior portions of the second integration plate, and an optional rounded edge of the interbody spinal implant may each comprise a soft tissue surface having a substantially smooth surface including nano features.

The present invention also encompasses a process of fabricating a predetermined surface topography. The process may include macro processing at least one integration surface, micro processing at least one integration surface and at least one graft contact surface, and nano processing at least one integration surface, at least one graft contact surface, and at least one soft tissue surface. The macro, micro, and nano process may include mechanical or chemical removal of at least a portion of the surface. For example, the nano process may include mild chemical etching, laser or other directed energy material removal, abrasion, blasting, or tumbling, followed by cleaning.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also facilitate osteointegration (e.g., formation of direct structural and functional interface between the artificial implant and living bone or soft tissue) with the surrounding living bone.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells upon the implant surface. Still further, it appears that these cells attach more readily to relatively rough surfaces rather than smooth surfaces. In this manner, a surface may be bioactive due to its ability to stimulate cellular attachment and osteointegration.

Implant Structure

Figure 1:
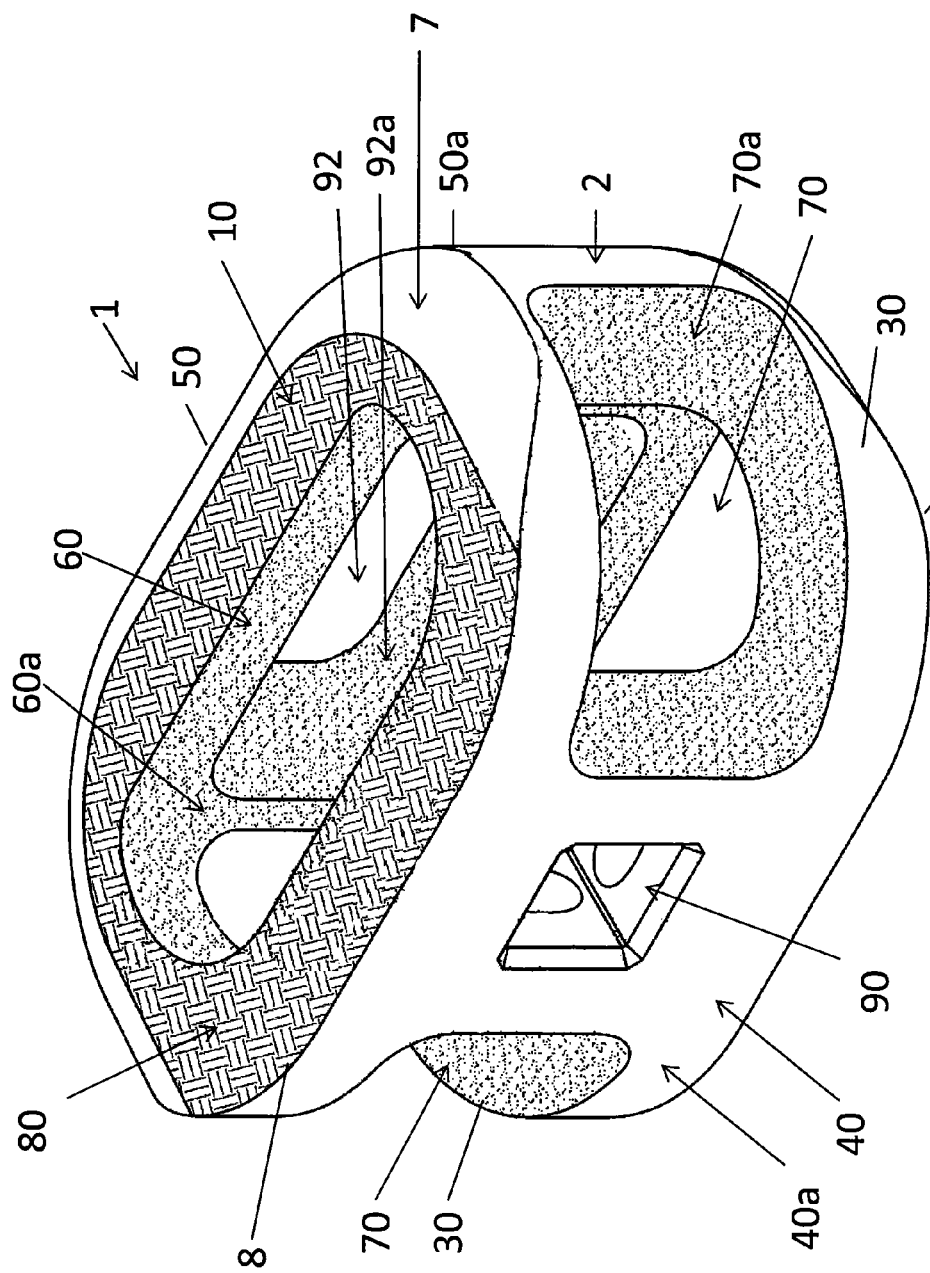
FIG. 1 shows a perspective view of an embodiment of the interbody spinal implant having three distinct surfaces.
Figure 2A:
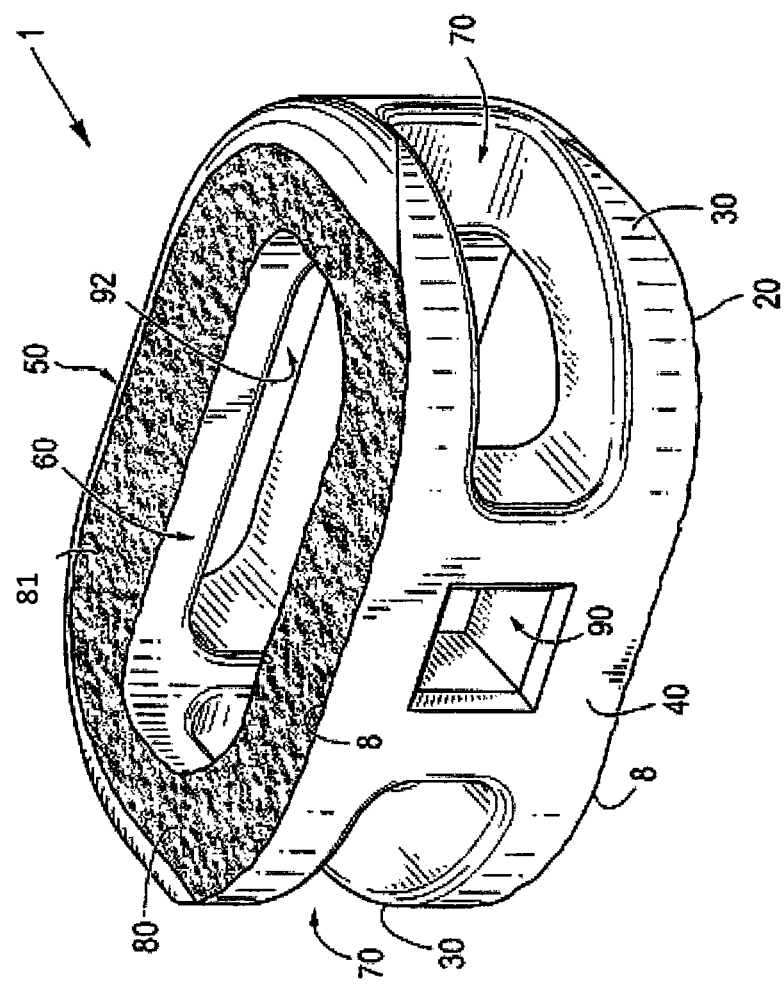
FIG. 2A shows a perspective view of an embodiment of the interbody spinal implant having a generally oval shape and roughened surface topography on the top surface.
Figure 2B:
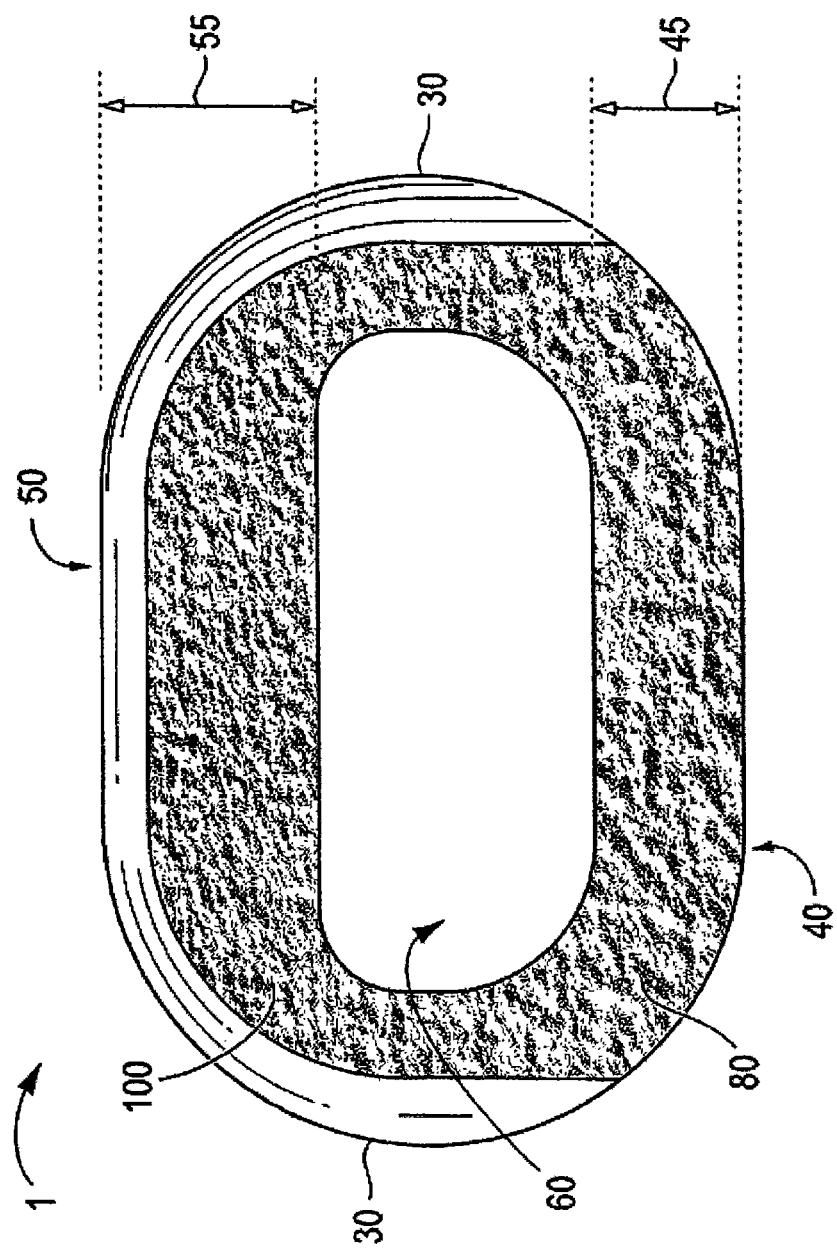
FIG. 2B shows a top view of the embodiment of the interbody spinal implant illustrated in FIG. 2A.

Referring now to the drawing, in which like reference numbers refer to like elements throughout the various figures that comprise the drawing, FIGS. 1 and 2A show a perspective view of a first embodiment of the interbody spinal implant 1 especially well adapted for use in an ALIF procedure. The interbody spinal implant 1 includes a body 2 having a top surface 10, a bottom surface 20, opposing lateral sides 30, and opposing anterior 40 and posterior 50 portions. The interbody spinal implant 1 may include implants made of a single piece of material or composite implants.

Interbody spinal implants 1 made of a single piece of material do not include integration plates 82. Thus, the integration surface may include the top surface 10 of the body 2 of the implant 1, the bottom surface 20 of the body 2 of the implant 1, or both. The integration surfaces have a roughened surface topography 80 including macro features, micro features, and nano features, without sharp teeth that risk damage to bone structures. The implant 1 may be composed of a suitable biocompatible material. In an exemplary embodiment, implant 1 is formed of metal. The metal may be coated or not coated. Suitable metals, such as titanium, aluminum, vanadium, tantalum, stainless steel, and alloys of those metals, may be selected by one of ordinary skill in the art. In a preferred embodiment, however, the metal is at least one of titanium, aluminum, and vanadium, without any coatings. In a more preferred embodiment, the implant 1 is comprised of titanium or a titanium alloy. An oxide layer may naturally form on a titanium or titanium alloy. Titanium and its alloys are generally preferred for certain embodiments of the present invention due to their acceptable, and desirable, strength and biocompatibility. In this manner, certain embodiments of the present interbody spinal implant 1 may have improved structural integrity and may better resist fracture during implantation by impact.

Figure 3:
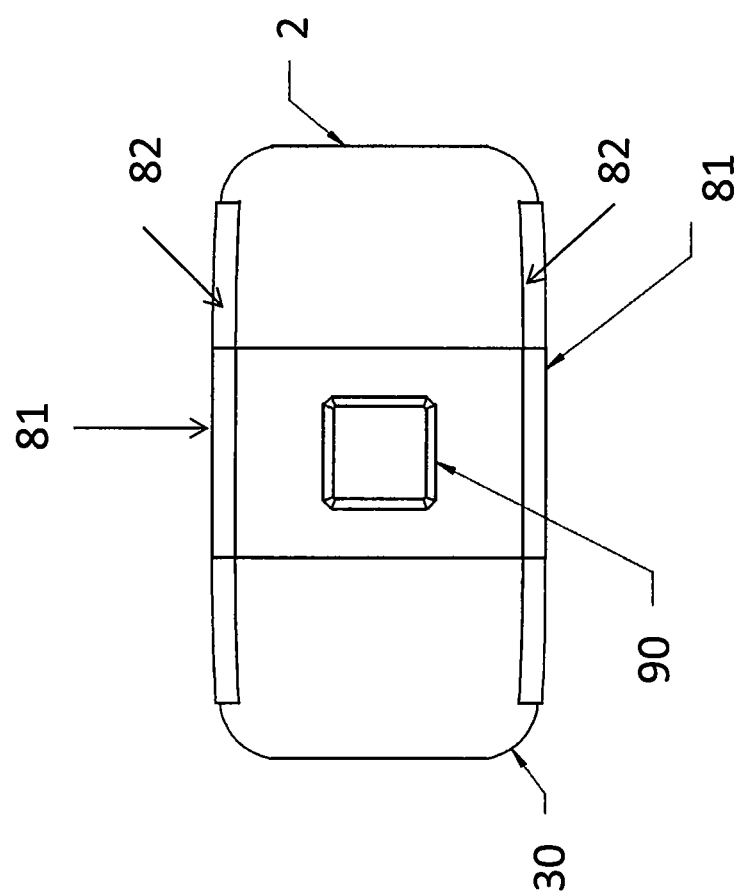
FIG. 3 shows an anterior view of an embodiment of the interbody spinal implant having two integration plates, which sandwich the body of the implant.
Figure 6:
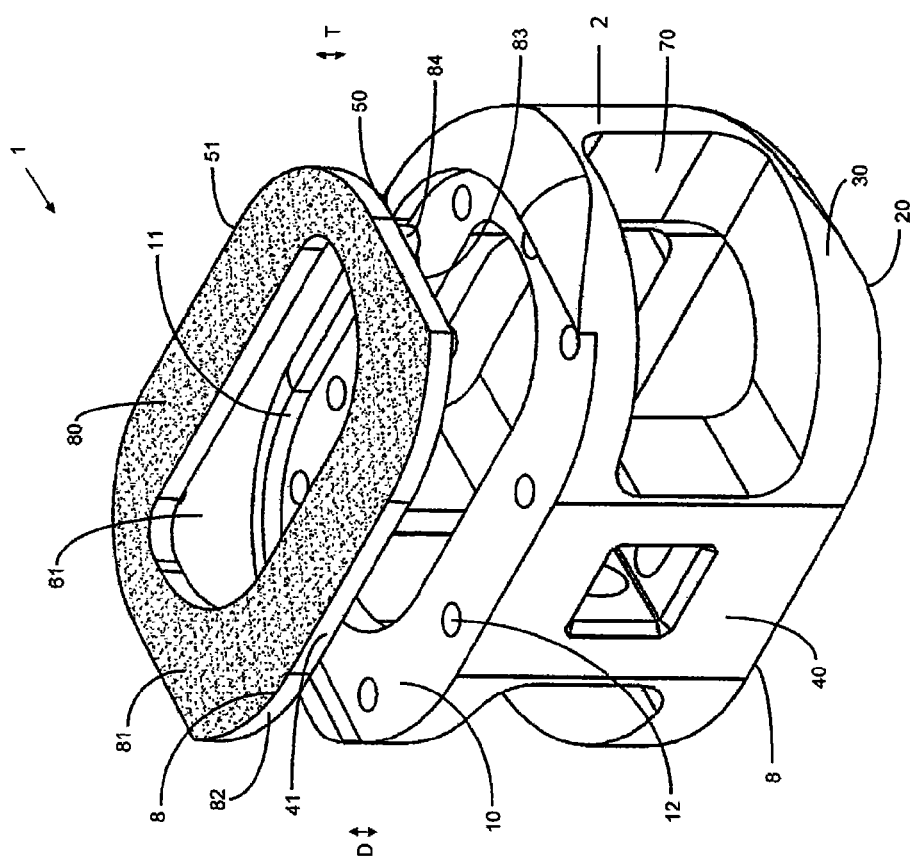
FIG. 6 shows an exploded view of a generally oval-shaped implant with an integration plate.

Composite implants include at least a body 2 and one or two integration plates 82, which may be formed from the same or different materials. As depicted in FIG. 6, the implant 1 includes a first integration plate 82 affixed to the top surface 10 of the body 2 and an optional second integration plate 82 (shown in FIG. 3) affixed to the bottom surface 20 of the body 2. The first integration plate 82 and optional second integration plate 82 each have a top surface 81, a bottom surface 83, opposing lateral sides, opposing anterior portion 41 and posterior portion 51, and a single vertical aperture 61 extending from the top surface 81 to the bottom surface 83 and aligning with the single vertical aperture 60 of the body 2.

When present, the integration plate(s) 82 comprise an integration surface (e.g., the top surface 81 of the integration plate 82), which is adapted to grip bone through friction generated when the implant 1 is placed between two vertebrae and to inhibit migration of the implant 1 once implanted. The integration surfaces may also have a fusion and biologically active surface geometry. In other words, at least a portion of the top surface 81 of the first integration plate 82 (e.g., a first integration surface) and optionally a top surface 81 of a second integration plate 82 (e.g., a second integration surface) has a roughened surface topography 80 including macro features, micro features, and nano features, without sharp teeth that risk damage to bone structures. The roughened surface topography 80 may include macro features, micro features, and nano features of a regular repeating pattern, which may promote biological and chemical attachment or fusion with the bone structure.

The body 2 and at least one integration plate 82 are preferably compatibly shaped, such that the implant 1 having the body 2 and integration plate(s) 82 joined together may have a generally oval shape, a generally rectangular shape, a generally curved shape, or any other shape described or exemplified in this specification. Thus, for example, the body 2 and the integration plate(s) 82 may be generally oval-shaped in transverse cross-section. The body 2 and the integration plate (s) 82 may be generally rectangular-shaped in transverse cross-section. The body 2 and the integration plate(s) 82 may be generally curved-shaped in transverse cross-section.

The body 2 and integration plate(s) 82 of the implant 1 may be the same material or may be different. The body 2 and the integration plate(s) 82 may be composed of a suitable biocompatible material. In an exemplary embodiment, the body 2 and optional integration plate(s) 82 are formed of metal, which may be coated or not coated. Suitable metals, such as titanium, aluminum, vanadium, tantalum, stainless steel, and alloys of the metals, may be selected by one of ordinary skill in the art. In a preferred embodiment, however, the metal is at least one of titanium, aluminum, and vanadium, without any coatings. In a more preferred embodiment, the body 2 and optional integration plate(s) 82 are comprised of titanium or a titanium alloy. An oxide layer may naturally form on a titanium or titanium alloy.

Alternatively, the body 2 may be composed of a non-metal biocompatible material. In one embodiment, the body 2 of the implant 1 is formed of a plastic, polymeric, or composite material. For example, suitable polymers may comprise silicones, polyolefins, polyesters, polyethers, polystyrenes, polyurethanes, acrylates, and co-polymers and mixtures of the polymers. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body 2 comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Certain embodiments of the interbody spinal implant 1 are substantially hollow and have a generally oval-shaped transverse cross-sectional area. Substantially hollow, as used in this document, means at least about 33% of the interior volume of the interbody spinal implant 1 is vacant. Still further, the substantially hollow portion may be filled with cancellous autograft bone, allograft bone, demineralized bone matrix (DBM), porous synthetic bone graft substitute, bone morphogenic protein (BMP), or combinations of those materials.

The anterior portion 40, or trailing edge, of the implant 1 is preferably generally greater in height than the opposing posterior portion 50. Accordingly, the implant 1 may have a lordotic angle to facilitate sagittal alignment. The implant 1 may better compensate, therefore, for the generally less supportive bone found in the posterior regions of the vertebral endplate. The posterior portion 50 of the interbody implant 1, preferably including the posterior-lateral corners, may also be highly radiused, thus allowing for ease of implantation into the disc space. Thus, the posterior portion 50 may have a generally blunt nosed profile. The anterior portion 40 of the implant 1 may also preferably be configured to engage a delivery device, driver, or other surgical tool (and, therefore, may have an opening 90).

As illustrated in FIG. 2A, the anterior portion 40 of the implant 1 is substantially flat. Thus, the anterior portion 40 provides a face that can receive impact from a tool, such as a surgical hammer, to force the implant 1 into position. The implant 1 has a sharp edge 8 where the anterior portion 40 meets the top surface 10, where the anterior portion 40 meets the bottom surface 20, or in both locations. The sharp edge or edges 8 function to resist pullout of the implant 1 once it is inserted into position.

Three Distinct Surfaces of the Implant

The three surfaces of the implant 1 are designed to balance friction with roughened integration surfaces, preserve critical tissues and influence the natural biological responses of cells forming bone structures in contact with the outer smooth soft tissue surfaces, and enhance healing of joint space fusion treatments by providing graft contact surfaces. The at least three distinct surfaces described in this document may also better promote the osteointegration of certain embodiments of the present invention. The roughened surface topography 80 of the integration surfaces may better grip the vertebral endplate surfaces and inhibit implant migration upon placement and seating. The coarse surface topography of the graft contact surface may positively promote naturally occurring biological bone remodeling and fusion responses, for example, by stabilizing the graft materials and transferring loads from the motion of the joint through the implant body to those graft materials. The smooth surface topography of the soft tissue surface may provide an anchoring point and signaling function to bone forming cells to positively influence the fusion and healing responses. In addition, the smooth surface topography functions as a low friction surface so as to not cause unintentional abrasion or laceration of delicate soft tissue that the implant may contact during or after insertion.

(a) Integration Surfaces

Figure 5A:
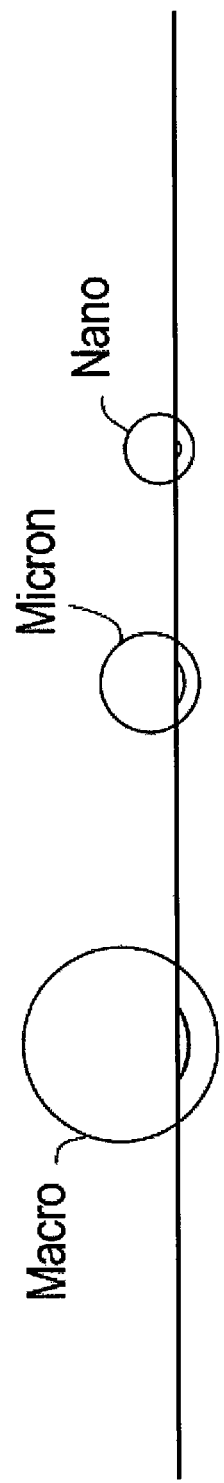
FIG. 5A represents macro-, micro-, and nano-scaled features on a surface.

The implant 1 includes a roughened surface topography 80 or integration surface on at least a portion of the top surface, bottom surface, or both (e.g., the top surface 81 of an integration plate 82). As used in this document, the integration surface is the surface at least partially in contact with the vertebral or bone structure. In one embodiment of the present invention, the roughened surface topography 80 is obtained by combining separate macro processing, micro processing, and nano processing steps. The term "macro" typically means relatively large; for example, in the present application, dimensions measured in millimeters (mm). The term "micro" typically means one millionth ($10^{-6}$); for example, in the present application, dimensions measured in microns (μm) which correspond to $10^{-6}$ meters. The term "nano" typically means one billionth ($10^{-9}$); for example, in the present application, dimensions measured in nanometers (nm) which correspond to $10^{-9}$ meters. FIG. 5A depicts macro, micro, and nano-sized surface features on a surface.

The interbody implant 1 has a roughened surface topography 80 on the integration surface(s). The integration surface may include the top, bottom, or both surfaces of the implant. In the case of no integration plates 82, this would include the top 10, bottom 20, or both surfaces of the body 2 of the implant 1. In the case of one integration plate 82 affixed to the top 10 of the body 2 of the implant, this would include the top 81 of the integration plate 82, the bottom 20 of the body 2, or both surfaces. In the case of one integration plate 82 affixed to the bottom 20 of the body 2 of the implant 1, this would include the top 10 of the body 2, the top 81 of the integration plate 82 (i.e., the outer surface of the integration plate 82 at the bottom of the implant), or both surfaces. In the case of two integration plates 82 sandwiched around the body 2 of the implant 1, this would include the top 81 of the first integration plate 82, the top 81 of the second integration plate 82, or both surfaces (i.e., the outer surfaces of both integration plates 82 at the top and bottom of the implant, respectively).

The integration surface(s) comprise predefined surface features that (a) engage the vertebral endplates with a friction fit and, following an endplate preserving surgical technique, (b) attain initial stabilization, and (c) benefit fusion. The composition of the endplate is a thin layer of notch-sensitive bone that is easily damaged by features (such as teeth) that protrude sharply from the surface of traditional implants. Avoiding such teeth and the attendant risk of damage, the roughened surface topography 80 of the integration surface(s) does not have teeth or other sharp, potentially damaging structures; rather, the roughened surface topography 80 may have a pattern of repeating features of predetermined sizes, smooth shapes, and orientations. As used in the document, "predetermined" means determined beforehand, so that the predetermined characteristic must be determined, i.e., chosen or at least known, before use of the implant 1.

The shapes of the frictional surface protrusions of the roughened surface topography 80 are formed using processes and methods commonly applied to remove metal during fabrication of implantable devices such as chemical, electrical, electrochemical, plasma, or laser etching; cutting and removal processes; casting; forging; machining; drilling; grinding; shot peening; abrasive media blasting (such as sand or grit blasting); and combinations of these subtractive processes. Additive processes such as welding, thermal, coatings, sputtering, and optical melt additive processes are also suitable. The resulting surfaces either can be random in the shape and location of the features or can have repeating patterns. This flexibility allows for the design and production of surfaces that resist motion induced by loading in specific directions that are beneficial to the installation process and resist the opposing forces that can be the result of biologic or patient activities such as standing, bending, or turning or as a result of other activities. The shapes of the surface features, when overlapping, work to increase the surface contact area but do not result in undercuts that generate a cutting or aggressively abrasive action on the contacting bone surfaces.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allow for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous method.

The first step in the process may be mechanical (e.g., machining though conventional processes) or chemical bulk removal, for example, to generate macro features. The macro features may be of any suitable shape, for example, roughly spherical in shape, without undercuts or protruding sharp edges. Other shapes are possible, such as ovals, polygons (including rectangles), and the like. These features may be at least partially overlapped with the next scale (micro) of features using either chemical or mechanical methods (e.g., $AlO_2$ blasting) in predetermined patterns which also do not result in undercuts or protruding sharp edges. The third and final process step is completed through more mild (less aggressive) etching (e.g., HCl acid etching) that, when completed, generates surface features in both the micro and nano scales over both of the features generated by the two previous steps. The nano layer may dictate the final chemistry of the implant material.

(b) Graft Contact Surfaces

The graft contact surface includes micro and nano features, which positively influence naturally occurring biological bone remodeling and fusion responses. Such results may occur by stabilizing the graft materials and transferring loads from the motion of the joint through the implant body to these materials. The graft contact surface may include surfaces that are in contact with or may become in contact with contained bone growth inducing materials. For example, the substantially hollow portion of the implant 1 may be filled with bone growth inducing materials once the implant 1 has been inserted into position. Suitable bone growth inducing materials may include, but are not limited to, cancellous autograft bone, allograft bone, demineralized bone matrix (DBM), porous synthetic bone graft substitute, bone morphogenic protein (BMP), and combinations of those materials.

The graft contact surface may include the interior surfaces of the implant 1. In other words, the graft contact surfaces may include any surfaces that may be in contact with bone growth inducing materials (once added to the inside of the implant). In particular, the surfaces typically in contact with bone growth inducing materials include one or more surfaces defined by the single vertical aperture 60, one or more surfaces defined by at least one transverse aperture 70, and one or more surfaces defined by one or more alternative openings 92 in the implant 1. In an exemplary embodiment depicted in FIG. 1, the graft contact surfaces include each of surface 60a defined by the single vertical aperture 60, surfaces 70a defined by two transverse apertures 70, and surface 92a defined by alternative opening 92.

The graft contact surface may have a "coarse" surface topography in that the surface topography is roughened or textured in the microscopic and nanoscopic levels. The micro features may be formed using either chemical or mechanical methods (e.g., $AlO_2$ blasting) in predetermined patterns, which also do not result in undercuts or protruding sharp edges. The nano features may be formed through more mild (less aggressive) etching (e.g., HCl acid etching). The graft contact surface may have a mid-level of friction when evaluated in comparison to the integration surface and the soft tissue surface. In other words, a frictional relationship (e.g., a coefficient of friction) between the integration surface, the graft contact surface, and the soft tissue surface may be defined as follows: the integration surface≥the graft contact surface≥the soft tissue surface.

(c) Soft Tissue Surfaces

The soft tissue surface or insertion surface includes a low friction surface with nano features (and optionally micro features) to avoid unintentional laceration or abrasion of delicate soft tissues the implant 1 contacts during insertion, after insertion, or both. The soft tissue surface can also provide an anchoring point and signaling function to bone forming cells in order to positively influence the fusion and healing processes.

The soft tissue surface may include the exterior surfaces of the implant 1, except for the integration surface. In other words, other than the one or more integration surfaces, the soft tissue surfaces may include any outer surfaces which may contact bone or soft tissues during or after implantation. In particular, the soft tissue surface may include the opposing lateral sides 30 of the body 2, the opposing anterior portion 40 of the body 2, and the posterior portion 50 of the body 2. In the case of one integration plate 82, the soft tissue surface may additionally include the opposing lateral sides of the integration plate 82, the opposing anterior portion 41 of the integration plate 82, and the posterior portion 51 of the integration plate 82. In the case of two integration plates 82, the soft tissue surface may include the opposing lateral sides of both integration plates 82 and the opposing anterior portion 41 and posterior portion 51 of both integration plates 82. The soft tissue surface may also include any rounded edges 7 on the interbody spinal implant including rounded edges 7 on the body 2 or either or both of the integration plates 82.

The soft tissue surface may have a "smooth" surface topography in that the surface topography appears substantially smooth to the unaided eye. The smooth surface may include, however, intentional nano-sized features, and optionally, micro features. The nano features, and optionally, the micro features, may be formed through more mild (less aggressive) etching (e.g., HCl acid etching), for example. The soft tissue surface may have a low degree of friction when evaluated in comparison to the integration surface and the soft tissue surface. In other words, a frictional relationship (e.g., a coefficient of friction) between the integration surface, the graft contact surface, and the soft tissue surface may be defined as follows: a high degree of friction for the integration surface relative to a medium degree of friction for the graft contact surface relative to a low degree of friction for the soft tissue surface.

Macro, Micro, and Nano Processes

Figure 11:
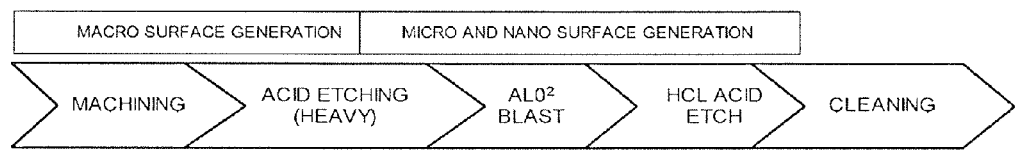
FIG. 11 illustrates one set of process steps that can be used to form macro, micro, or nano processes.

FIG. 11 illustrates one set of process steps that can be used to form macro, micro, or nano processes. As illustrated, there may be some overlap in the processes that can be applied to form each of the three types of features (macro, micro, and nano). For example, acid etching can be used to form the macro features, then the same or a different acid etching process can be used to form the micro features. The features may be provided in a random design or a predetermined pattern (e.g., a repeating pattern).

(a) Macro Features

The macro features are relatively large features (e.g., on the order of millimeters). The macro features may be formed from subtractive techniques (e.g., mechanical or chemical bulk removal, for example) or additive techniques (e.g., deposition). Preferably, the macro features are formed by subtractive techniques, which remove at least portions of the surface (e.g., from the titanium material that was used to form the part). Suitable subtractive techniques may include for example, machining (e.g., machine tools, such as saws, lathes, milling machines, and drill presses, are used with a sharp cutting tool to physically remove material to achieve a desired geometry) or unmasked or masked etching (e.g., portions of the surface is protected by a masking material which resists etching and an etching substance is applied to unmasked portions). The patterns may be organized in regular repeating patterns and optionally overlapping each other. In a preferred embodiment, the macro features may be formed in three, sequential steps.

Figure 4A:
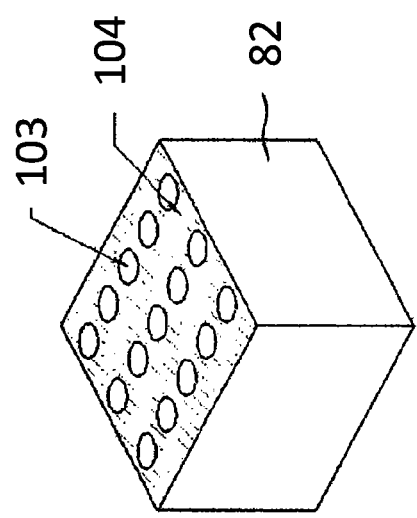
FIGS. 4A-4C depict a technique to form the macro features of the roughened surface topography on the integration surface in an embodiment of the invention.

FIG. 4A illustrates the result of the first step in limning the macro features 102. Specifically, a first cut pattern 103 of the macro features is formed in a surface (e.g., the top surface 81 of the integration plate 82). The "cut 1" features of the first cut pattern 103 may cover about 20% of the total area of the surface, for example, leaving about 80% of the original surface 104 remaining. The range of these percentages may be about ±20%, preferably ±10%, and more preferably about ±5%. The "cut 1" features of the first cut pattern 103 do not have any undercuts. In one embodiment, these "cut 1" features have the smallest diameter and greatest depth of the macro features that are formed during the sequential steps.

Figure 4B:
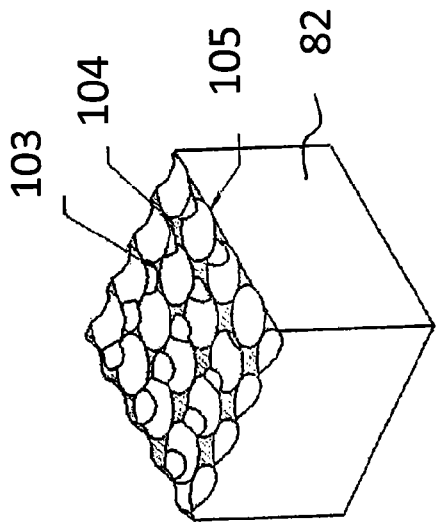

FIG. 4B illustrates the result of the second step in forming the macro features. Specifically, a second cut pattern 105 of the macro features is formed in the surface. Together, the "cut 1" features of the first cut pattern 103 and the "cut 2" features of the second cut pattern 105 may cover about 85% of the total area of the surface, for example, leaving about 15% of the original surface 104 remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of forming the macro features.

Figure 4C:
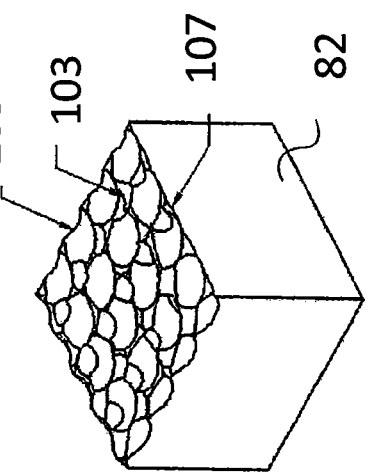

FIG. 4C illustrates the result of the third and final step in forming the macro features. Specifically, a third cut pattern 107 of the macro features may be formed in the surface. Together, the "cut 1" features of the first cut pattern 103, the "cut 2" features of the second cut pattern 105, and the "cut 3" features of the third cut pattern 107 cover about 95% of the total area of the surface, for example, leaving about 5% of the original surface 104 remaining. The range of these percentages may be about ±1%. In an embodiment of the invention, these "cut 3" features may have the largest diameter and least depth of the macro features that are formed during the sequential process steps.

Figure 4D:
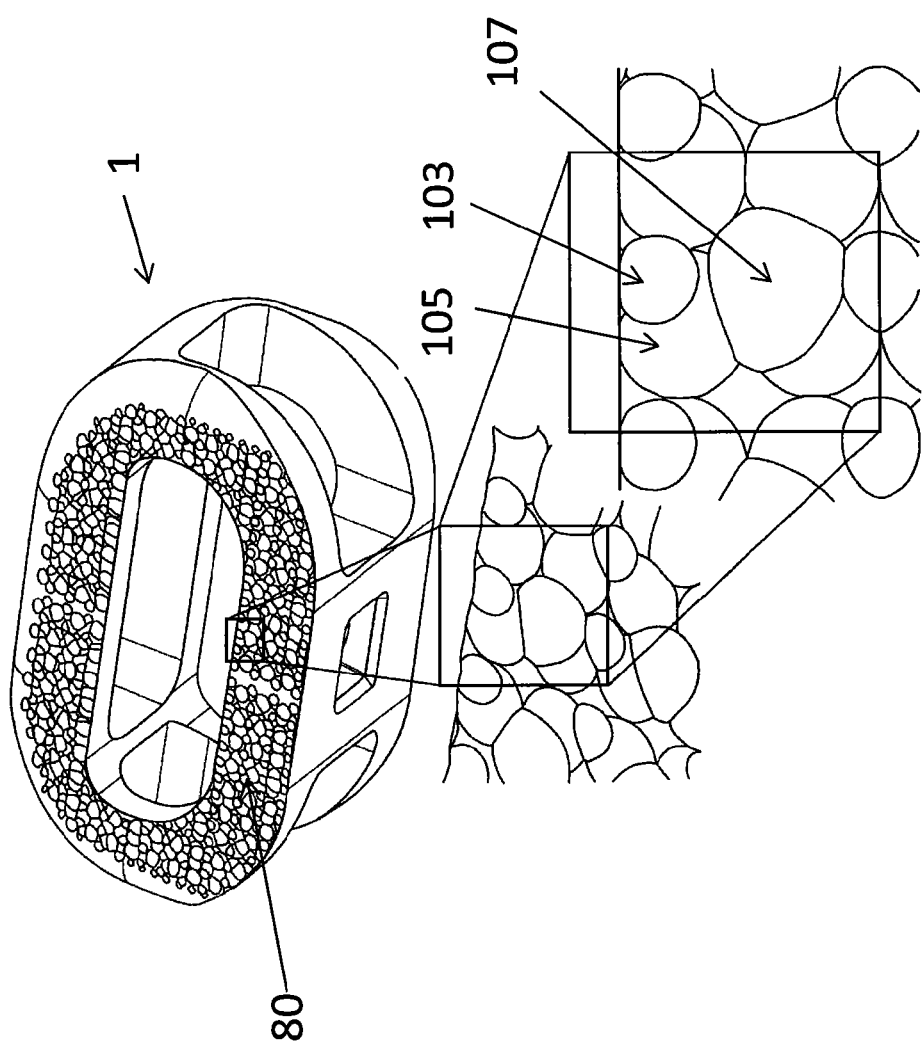
FIG. 4D depicts the macro features of the roughened surface topography on the integration surface in an embodiment of the invention.

FIG. 4D also depicts the roughened surface topography 80 of the integration surface on the implant 1 following completion of the three, sequential processing steps. As shown, the finished macro features comprise multiple patterns of the three, overlapping cuts: the first cut pattern 103, the second cut pattern 105, and the third cut pattern 107.

(b) Micro Features

Depending on the surface structure desired, the micro surface features (e.g., on the order of micrometers) may be applied to all or a portion of the surface (for example, to the integration surface, the graft contact surface, the soft tissue surfaces, or all three). The micro features may also be formed from subtractive techniques (e.g., mechanical or chemical bulk removal, for example) or additive techniques (e.g., deposition). Preferably, the micro features are also formed by subtractive techniques.

In an exemplary embodiment, the micro features are cut by masked or unmasked etching, such as acid etching. For example, portions of the surface, optionally including portions of the surface exposed by the macro step(s) described above for the case of the integration surface, may be exposed to a chemical etching. In an exemplary embodiment, the micro process includes an acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The etching process may be repeated a number of times as necessitated by the amount and nature of the irregularities required for any particular application. Control of the strength of the etchant material, the temperature at which the etching process takes place, and the time allotted for the etching process allows fine control over the resulting surface produced by the process. The number of repetitions of the etching process can also be used to control the surface features. For example, the micro features may be obtained via the repetitive masking and chemical or electrochemical milling processes described in U.S. Pat. No. 5,258,098; 5,507,815; 5,922,029; and 6,193,762, the contents of which are incorporated by reference into this document, in their entirety, and for all purposes.

By way of example, an etchant mixture of at least one of nitric acid and hydrofluoric acid may be repeatedly applied to a titanium surface to produce an average etch depth of about 0.53 mm. In another example, chemical modification of a titanium surface can be achieved using at least one of hydrofluoric acid, hydrochloric acid, and sulfuric acid. In a dual acid etching process, for example, the first exposure may be to hydrofluoric acid and the second may be to a hydrochloric acid and sulfuric acid mixture. Chemical acid etching alone may enhance osteointegration without adding particulate matter (e.g., hydroxyapatite) or embedding surface contaminants (e.g., grit particles).

The micro features may also be cut by abrasive or grit blasting, for example, by applying a stream of abrasive material (such as alumina, sand, and the like) to the surface. The abrasive material may include inert and non-bioactive materials. Alternatively, the abrasive material may include those reactive with biological functions as part of healing and fusions. In an exemplary embodiment, the micro features are created, at least partially, with an aqueous hydrochloric acid etching step and at least partially with an $AlO_2$ blasting step. Patterns may be organized in regular repeating patterns and optionally overlapping each other. After the micro features are formed, it is possible that less than about 3% of the original surface 104 remains. The range of that percentage may be about ±1%.

(c) Nano Features

Depending on the surface structure desired, the nano surface features (e.g., on the order of nanometers) may be applied to all or a portion of the surface (for example, to the integration surface, the graft contact surface, the soft tissue surfaces, or all three). The nano features may also be formed from subtractive techniques (e.g., mechanical or chemical bulk removal, for example) or additive techniques (e.g., deposition). Preferably, the nano features are also formed by subtractive techniques.

In an exemplary embodiment, the nano features are cut by masked or unmasked etching. For example, portions of the surface, including optionally portions of the surface exposed by the macro and micro steps described above in the case of the integration surface, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching process for the nano step is preferably less aggressive than the acid etching process in the micro step. In other words, a less acidic, mild, or more diluted acid may be selected. In an exemplary embodiment, the nano features are created, at least partially, with an aqueous hydrochloric acid etching step.

As an example, the nano features may be formed by preparing an acid solution comprising hydrochloric acid, water, and titanium; applying the acid solution to the desired surface; removing the acid solution by rinsing with water; and heating and subsequently cooling the surface being treated.

The acid solution may be prepared using any suitable techniques known in the art. For example, the acid solution may be prepared by combining hydrochloric acid and water, simultaneously or sequentially. The aqueous hydrochloric acid solution may optionally be heated, for example, to a temperature of about 150-250° F., preferably about 200-210° F., and most preferably about 205° F. The titanium may be seeded (e.g., added) in the aqueous hydrochloric acid solution or may already be present from titanium previously removed from at least one surface of the implant, for example, in a continuous manufacturing process. The solution may optionally be cooled. The acid solution may comprise a concentration of 20-40% hydrochloric acid, preferably about 25-31% hydrochloric acid, and more preferably about 28% hydrochloric acid, based on the weight percent of the solution.

It is preferred that the etch rate is substantially constant. The etch rate in a metal-free solution is typically erratic. For example, the metal may be passive for some period and then suddenly start reacting (sometimes at an exceptionally high rate), then may even go passive again. Therefore, it is preferred that the metal (e.g., titanium) is present from the manufacturing process or the titanium is seeded with the aqueous hydrochloric acid solution.

The acid solution may be applied to the surface (e.g., a treated surface) using any suitable mechanism or techniques known in the art, for example, immersion, spraying, brushing, and the like. In an exemplary embodiment, the acid solution is applied to the surface by immersing the entire part (e.g., the integration plate 82) in the solution. It is also contemplated that the part (e.g., the integration plate 82) may be immersed in the acid solution alone or in combination with the entire implant 1 or the assembled implant 1 (i.e., including the body 2). If desired, certain areas of the surface or the implant 1 may be masked in patterns to protect certain portions of the implant 1. The acid solution may be heated when it is applied to the surface. For example, the solution may be heated to a temperature of about 150-250° F., preferably about 200-210° F., and most preferably about 205° F. The solution may also be applied for any suitable period of time. For example, the solution may be applied to the surface for a period of time of about 5-30 minutes, preferably about 15-25 minutes, and more preferably about 20 minutes.

After the acid solution is applied, the acid solution may be removed, for example, by rinsing with water (e.g., deionized water). The treated surface or the entire implant 1 may be subsequently dried. The treated surface may be dried using any suitable mechanism or techniques known in the art, for example, by heating in an oven (e.g., a dry oven). The treated surface (or entire implant) may be heated to a temperature of about 110-130° F., preferably about 120-125° F., and most preferably about 122.5° F. The treated surface (or entire implant) may be heated for any suitable period of time, for example about 30-50 minutes, preferably about 35-45 minutes, and more preferably about 40 minutes. After heating, the treated surface may be cooled to room temperature, for example.

It is contemplated that the nano features may also be removed by the abrasive or grit blasting, for example, described for the micro processing step. Patterns may be organized in regular repeating patterns and optionally overlapping each other. After the nano features are formed, it is possible that less than about 1% of the original surface 104 remains. For example, after the nano features are formed, the nano features (and optionally, the macro and micro features) may cover substantially the entire surface.

The nano features may also be achieved by tumble finishing (e.g., tumbling) the part or the implant 1. Suitable equipment and techniques can be selected by one of ordinary skill in the art. For example, a barrel may be filled with the parts or implants and the barrel is then rotated. Thus, the parts or implants may be tumbled against themselves or with steel balls, shot, rounded-end pins, ballcones, or the like. The tumbling process may be wet (e.g., with a lubricant) or dry.

As should be readily apparent to a skilled artisan, the process steps described in this document can be adjusted to create a mixture of depths, diameters, feature sizes, and other geometries suitable for a particular implant application. The orientation of the pattern of features can also be adjusted. Such flexibility is desirable, especially because the ultimate pattern of the surface topography desired, for example, the integration surface of the implant 1 may be oriented in opposition to the biologic forces on the implant 1 and to the insertion direction. In one particular embodiment, for example, the pattern of the roughened surface topography 80 may be modeled after an S-shaped tire tread. It is also contemplated that the same or different process steps may be used to create each of the macro, micro, and nano features on each of the desired surfaces.

Roughness Parameters

Figure 5B:
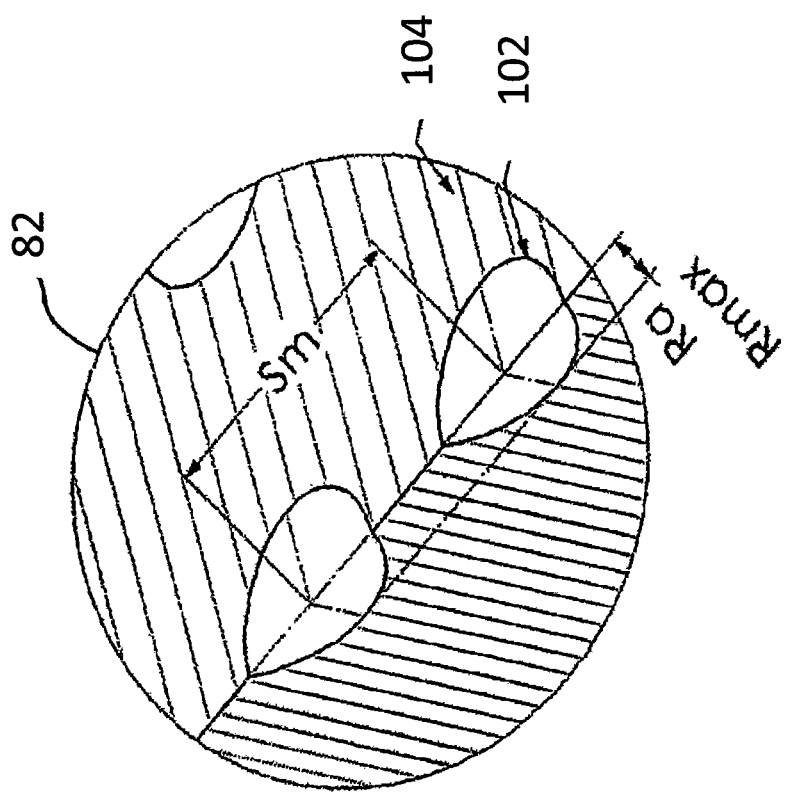
FIG. 5B shows Ra, Rmax, and Sm for a roughened surface topography.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Meanwhile, FIG. 5B illustrates all three parameters, namely, Ra, Rmax, and Sm, for the macro features 102 of the integration plate 82. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 12:
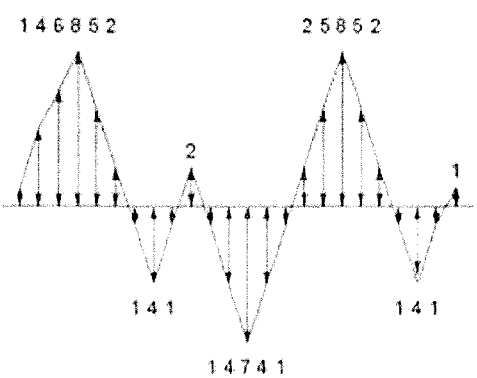
FIG. 12 graphically represents the average amplitude, Ra.

In practice, "Ra" is the most commonly used roughness parameter. It is the arithmetic average height. Mathematically, Ra is computed as the average distance between each roughness profile point and the mean line. In FIG. 12, the average amplitude is the average length of the arrows.

In mathematical terms, this process can be represented as $$Ra = \frac{1}{n}\sum_{i=1}^{n}|y_i|$$

2. Average Peak-to-Valley Roughness Rz

Figure 13:
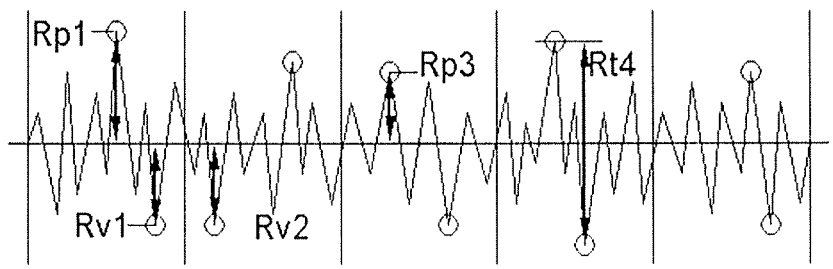
FIG. 13 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 13.

3. Maximum Peak-to-Valley Height Rmax

Figure 14:
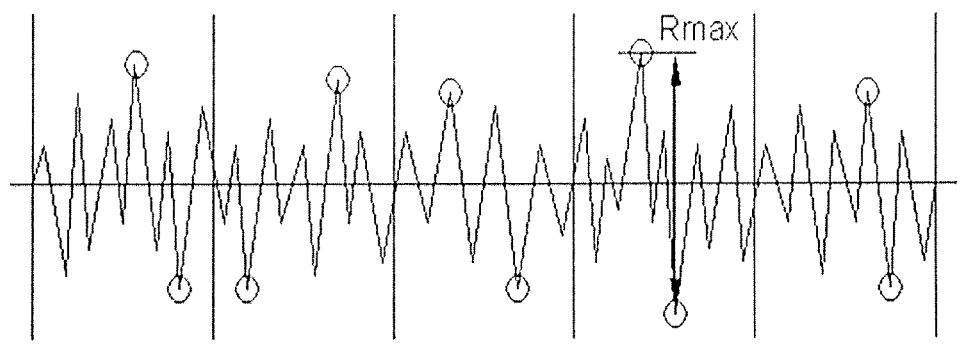
FIG. 14 graphically represents the maximum peak-to-valley height, Rmax.

The maximum peak-to-valley height, Rmax, is the maximum peak-to-valley distance in a single sampling length—as illustrated in FIG. 14.

4. Total Peak-to-Valley of Waviness Profile Wt

Figure 15:
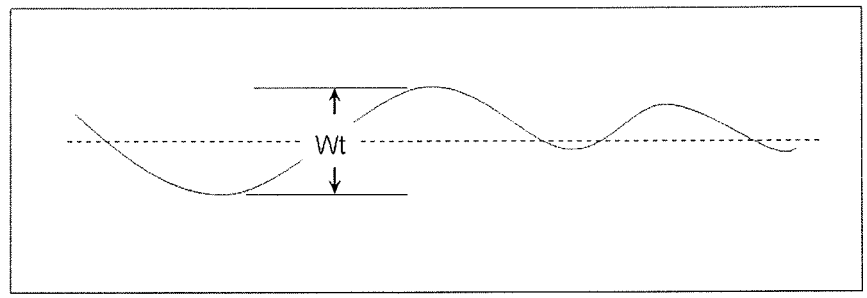
FIG. 15 graphically represents the total peak-to-valley waviness profile.

The total peak-to-valley of waviness profile (over the entire assessment length) is illustrated in FIG. 15.

5. Mean Spacing Sm

Figure 16:
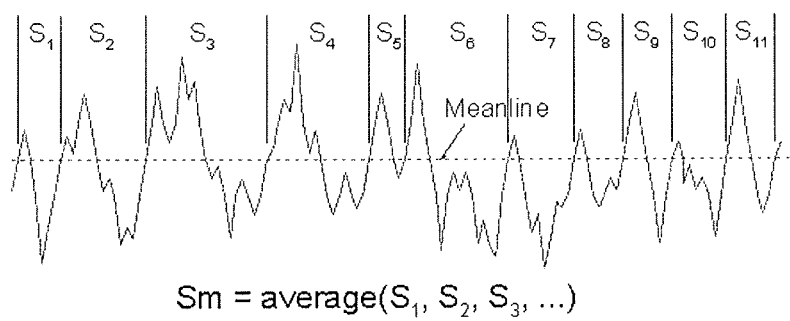
FIG. 16 graphically represents the mean spacing, Sm.

The mean spacing, Sm, is the average spacing between positive mean line crossings. The distance between each positive (upward) mean line crossing is determined and the average value is calculated, as illustrated in FIG. 16.

The parameters Sm, Rmax, and Ra can be used define the surface roughness following formation of each of the three types of features macro, micro, and nano.

The following preferred ranges (all measurements in microns) are as follows for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 8-200, preferably, 20-200, more preferably 50-150, and most preferably 100-125.

The following preferred ranges (all measurements in microns) are as follows for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, preferably 2-15, more preferably 4-10, even more preferably 2-8, and most preferably 2-6.

The following preferred ranges (all measurements in microns) are as follows for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-2, preferably 0.01-1, more preferably, 0.02-0.8, and most preferably 0.03-0.6.

An example of such data is provided in Table 2 below.

TABLE 2

EXAMPLE DATA BY PROCESS STEP

| | Size (Sm) | Depth (Rmax) | Roughness (Ra) |
|---|---|---|---|
| Surface Feature Size and Roughness (Metric): Macro (μm) | | | |
| Max. | 2,000 | 500 | 200 |
| Min. | 400 | 40 | 20 |
| Avg. | 1,200 | 270 | 110 |
| Surface Feature Size and Roughness (Metric): Micro (μm) | | | |
| Max. | 400 | 40 | 20 |
| Min. | 20 | 2 | 1 |
| Avg. | 210 | 11 | 5.5 |
| Surface Feature Size and Roughness (Metric): Nano (μm) | | | |
| Max. | 20 | 2 | 1 |
| Min. | 0.5 | 0.2 | 0.01 |
| Avg. | 10.25 | 1.1 | 0.505 |

Integration Plate and Attachment

In the case of a composite implant 1, 101, 101a, 201, and 301, the integration plate, shown in the drawing as component 82 (FIGS. 3 and 6), 182a (FIG. 7), 182 (FIG. 8), 382 (FIG. 9), and 282 (FIG. 10), respectively, includes the roughened surface topography 80, 180, 180a, 280, and 380 for the integration surface, and is connectable to either or both of the top surface 10, 110, 110a, 210, and 310 or bottom surface 20, 120, 120a, 220, and 320. The integration plate 82, 182, 182a, 282, and 382 includes a top surface 81, 181, 181a, 281, and 381; a bottom surface 83, 183, 183a, 283, and 383; an anterior portion 41, 141, 141a, 241, and 341; a posterior portion 51, 151, 151a, 251, and 351; and at least one vertical aperture 61, 161, 161a, 261, and 361. The anterior portion 41, 141, 141a, 241, and 341 preferably aligns with the anterior portion 40, 140, 140a, 240, and 340 of the main body 2 of the implant 1, 101, 101a, 201, and 301, respectively, and the posterior portion 51, 151, 151a, 251, and 351 aligns with the posterior portion 50, 150, 150a, 250, and 350 of the main body 2 of the implant 1, 101, 101a, 201, and 301, respectively. The vertical aperture 61, 161, 161a, 261, and 361 preferably aligns with the vertical aperture 60, 160, 160a, 260, and 360 of the main body 2 of the implant 1, 101, 101a, 201, and 301, respectively. Thus, the integration plate vertical aperture 61, 161, 161a, 261, and 361 and the body vertical aperture 60, 160, 160a, 260, and 360 preferably comprise substantially the same shape.

The integration plate 82, 182, 182a, 282, and 382 may be attached or affixed to the main body of the implant 1, 101, 101a, 201, and 301 using any suitable mechanisms known in the art. For example, the bottom surface 83, 183, 183a, 283, and 383 of the integration plate 82, 182, 182a, 282, and 382 may comprise a reciprocal connector structure, such as a plurality of posts 84, 184, 184a, 284, and 384 that align with and insert into a corresponding connector structure such as a plurality of holes 12, 112, 112a, 212, and 312 on the top surface 10, 110, 110a, 210, and 310 and/or bottom surface 20, 120, 120a, 220, and 320 of the main body 2 of the implant 1, 101, 101a, 201, and 301, respectively, and thus facilitate the connection between the integration plate 82, 182, 182a, 282, and 382 and the main body 2 of the implant 1, 101, 101a, 201, and 301. Thus, integration plates 82, 182, 182a, 282, and 382 with different sizes, shapes, or features may be used in connection with the implant 1, 101, 101*a*, 201, and 301, for example, to accommodate attributes of the spine of the patient to which the implant 1, 101, 101*a*, 201, and 301 is to be implanted. Among these different sizes, shapes, and features are lordotic angles; anti-expulsion edges 8, 108, 108*a*, 208, and 308; and anti-expulsion angles as described throughout this specification.

The implant 1, 101, 101*a*, 201, and 301 is configured to receive the integration plate 82, 182, 182*a*, 282, and 382, respectively. Thus, for example, the top surface 10, 110, 110*a*, 210, and 310 and/or bottom surface 20, 120, 120*a*, 220, and 320 of the implant 1, 101, 101*a*, 201, and 301 may be optionally recessed, and comprise a plurality of holes 12, 112, 112*a*, 212, and 312 that mate with the plurality of posts 84, 184, 184*a*, 284, and 384 on the bottom surface 83, 183, 183*a*, 283, and 383 of the integration plate 82, 182, 182*a*, 282, and 382. Thus, the plurality of posts 84, 184, 184*a*, 284, and 384 are inserted into the plurality of holes 12, 112, 112*a*, 212, and 312.

Figure 7:
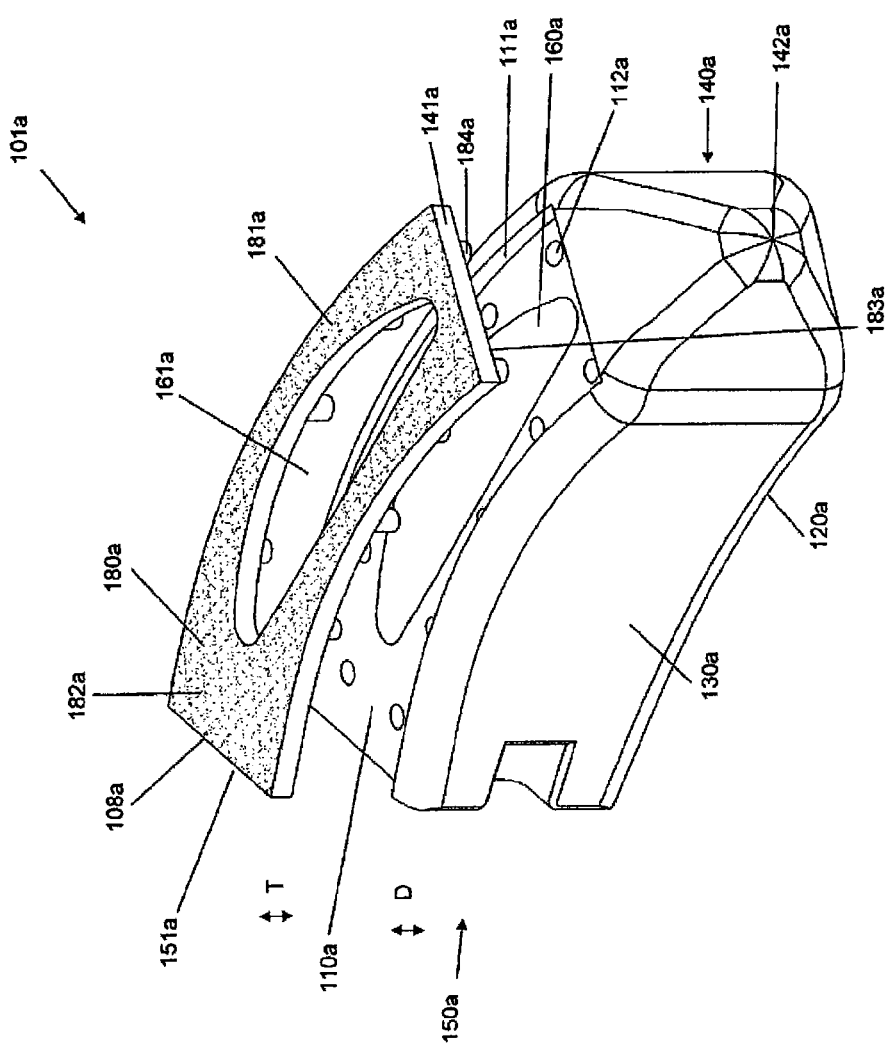
FIG. 7 shows an exploded view of a curved implant with an integration plate.
Figure 8:
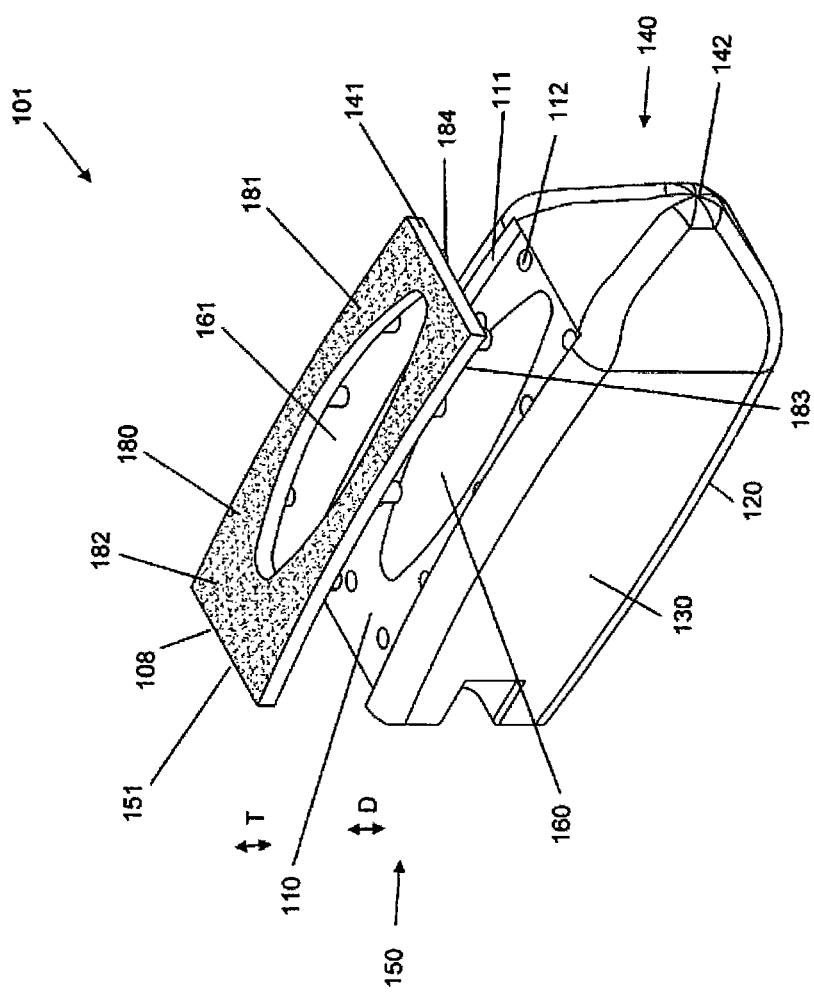
FIG. 8 shows an exploded view of a posterior implant with an integration plate.
Figure 9:
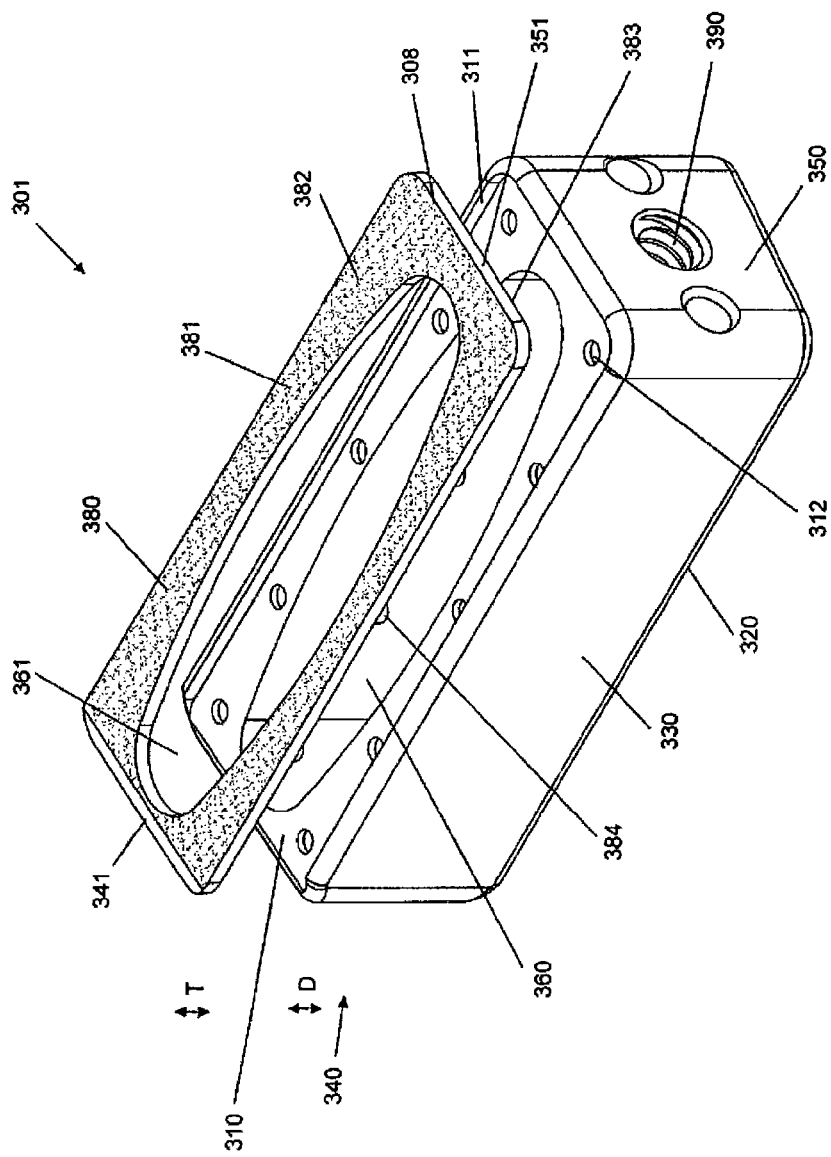
FIG. 9 shows an exploded view of a lateral lumbar implant with an integration plate.
Figure 10:
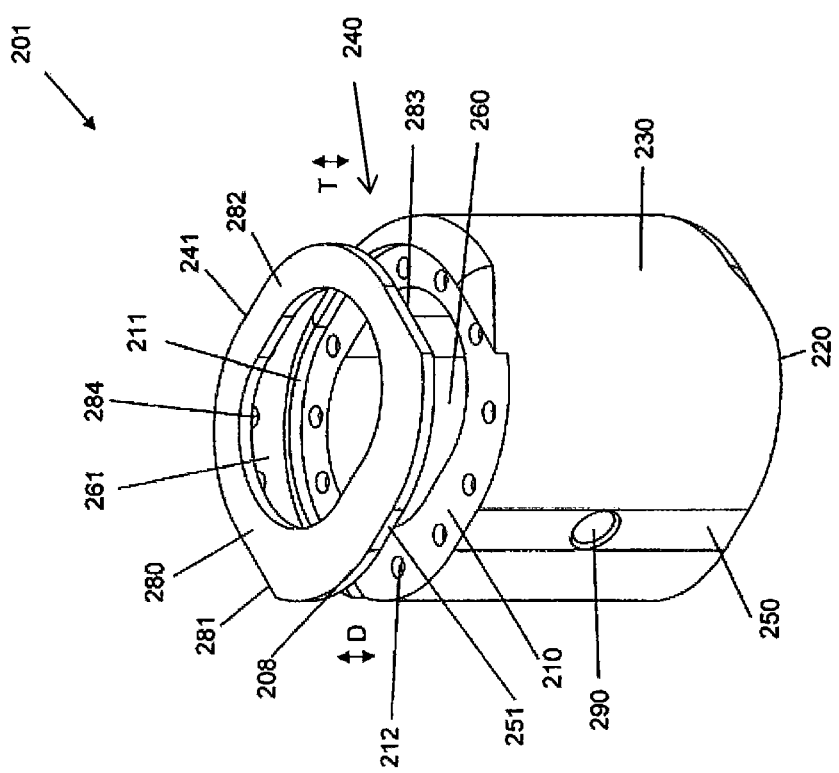
FIG. 10 shows an exploded view of a generally oval-shaped anterior cervical implant with an integration plate.

FIG. 1 shows that the top surface 10 is recessed and comprises a plurality of holes 12, but the recessed bottom surface 20 and its holes 12 are not shown. FIG. 6 shows that the top surface 110*a* is recessed and comprises a plurality of holes 112*a*, but the recessed bottom surface 120*a* and its holes 112*a* are not shown. FIG. 7 shows that the top surface 110 is recessed and comprises a plurality of holes 112, but the recessed bottom surface 120 and its holes 112 are not shown. FIG. 8 shows that the top surface 310 is recessed and comprises a plurality of holes 312, but the recessed bottom surface 320 and its holes 312 are not shown. FIG. 9 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110*a*, 210, and 310 and/or bottom surface 20, 120, 120*a*, 220, and 320.

The recess depth D preferably corresponds to a thickness T of the integration plate 82, 182, 182*a*, 282, and 382. Thus, in some aspects, the depth D and thickness T are the same so that once the integration plate 82, 182, 182*a*, 282, and 382 and body of the implant 1, 101, 101*a*, 201, and 301, respectively, are placed together, the top surface 10, 110, 110*a*, 210, and 310 and/or bottom surface 20, 120, 120*a*, 220, and 320 of the implant 1, 101, 101*a*, 201, and 301 is substantially even, at least at the seam/junction between the integration plate 82, 182, 182*a*, 282, and 382 and the top surface 10, 110, 110*a*, 210, and 310 or bottom surface 20, 210, 120*a*, 220, and 320. In some embodiments, the posterior portion 51, 151, 151*a*, 251, and 351 and the anterior portion 41, 141, 141*a*, 241, and 341 of the integration plate 82, 182, 182*a*, 282, and 382 have different thicknesses such that the anterior portion 41, 141, 141*a*, 241, and 341 has a greater thickness than the thickness of the posterior portion 51, 151, 151*a*, 251, and 351.

The recess depth D and the thickness T may each independently be from about 0.1 mm to about 10 mm. In preferred aspects, the recess depth D and the thickness T may each independently be from about 1 mm to about 5 mm. Thus, for example, the recess depth D or the thickness T may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 75 mm, or about 8 mm.

Recessing the top surface 10, 110, 110*a*, 210, and 310 or bottom surface 20, 120, 120*a*, 220, and 320 exposes a ridge 11, 111, 111*a*, 211, and 311 against which the anterior portion 41, 141, 141*a*, 241, and 341, posterior portion 51, 151, 151*a*, 251, and 251, or lateral side of the integration plate 82, 182, 182*a*, 282, and 382 may be seated when brought together with the implant 1, 101, 101*a*, 201, and 301.

The integration plate 82, 182, 182*a*, 282, and 382 may be used with an implant suitable for ALIF (e.g., implant 1, integration plate 82), PLIF (e.g., implant 101, integration plate 182), or TLIF fusion (e.g., implant 101*a*, integration plate 182*a*); may be used with an implant suitable for cervical fusion (e.g., implant 201, integration plate 282); and may be used with an implant suitable for lateral lumbar insertion (e.g., implant 301, integration plate 382).

The reciprocal connector such as the post 84, 184, 184*a*, 284, and 384 preferably is secured within the connector of the body such as the hole 12, 112, 112*a*, 212, and 312 to mediate the connection between the integration plate 82, 182, 182*a*, 282, and 382 and the implant 1, 101, 101*a*, 201, and 301. The connection should be capable of withstanding significant loads and shear forces when implanted in the spine of the patient. The connection between the post 84, 184, 184*a*, 284, and 384 and the hole 12, 112, 112*a*, 212, and 312 may comprise a friction fit. In some aspects, the reciprocal connector such as the post 84, 184, 184*a*, 284, and 384 and the connector of the body such as the hole 12, 112, 112*a*, 212, and 312 have additional compatible structures and features to further strengthen the connection between the integration plate 82, 182, 182*a*, 282, and 382 and the implant 1, 101, 101*a*, 201, and 301.

The structures and features may be on either or both of the integration plate 82, 182, 182*a*, 282, and 382 and the main body 2 of the implant 1, 101, 101*a*, 201, and 301. In general, the structures include fasteners, compatibly shaped joints, compatibly shaped undercuts, and/or other suitable connectors having different shapes, sizes, and configurations. For example, a fastener may include a pin, screw, bolt, rod, anchor, snap, clasp, clip, clamp, or rivet. In some aspects, an adhesive may be used to further strengthen any of the integration plate 82, 182, 182*a*, 282, and 382 and implant 1, 101, 101*a*, 201, and 301 connections described in this specification. An adhesive may comprise cement, glue, polymer, epoxy, solder, weld, or other suitable binding materials.

The integration plate 82, 182, 182*a*, 282, and 382 may comprise one or more reciprocal connectors (not shown), such as one or more posts, each having a bore, extending through a horizontal plane. The post may be inserted into a connector such as a hole through the implant 1, 101, 101*a*, 201, and 301. A fastener (not shown), such as a pin, may be inserted through the bore thereby preventing the post from being disengaged from the hole. In some aspects, the pin may be threaded through a second bore that passes through the walls of the implant 1, 101, 101*a*, 201, and 301 itself; although it is preferable that the implant 1, 101, 101*a*, 201, and 301 does not include a second bore through its walls and that the bore is accessible from the space inside of the implant. Alternatively, the integration plate 82, 182, 182*a*, 282, and 382 may comprise a plurality of bores (not shown) present on and having an opening accessible from the bottom of the integration plate 82, 182, 182*a*, 282, and 382. The bores may mate with a plurality of fasteners, which may comprise rods integral with or otherwise attached to the top surface or bottom surface of the implant 1, 101, 101*a*, 201, and 301. For example, the rods may be molded as upward-facing extensions or snap-fit into the bores. In some aspects, for example, where the body 2 of the implant 1, 101, 101*a*, 201, and 301 is comprised of a plastic or polymeric material, the hole 12, 112, 112*a*, 212, and 312 may not be present, and the screw or bolt (not shown) may be screwed directly into the plastic or polymeric material, with the screw threads tightly gripping the plastic or polymeric material to form the connection.

It is also contemplated that the bottom surface 83, 183, 183a, 283, and 383 of the integration plate 82, 182, 182a, 282, and 382 may comprise undercuts (not shown) in shapes that form a tight junction with compatible shapes on the implant 1, 101, 101a, 201, and 301. For example, the bottom surface 83, 183, 183a, 283, and 383 may comprise a dovetail joint, bevel, or taper that fits with a counterpart dovetail joint, bevel, or taper on the body 2 of the implant 1, 101, 101a, 201, and 301.

An adhesive (not shown) may directly join the integration plate 82, 182, 182a, 282, and 382 and the body 2 of the implant 1, 101, 101a, 201, and 301 together, with or without other connecting features. For example, the adhesive may be applied to the bottom surface 83, 183, 183a, 283, and 383 of the integration plate 82, 182, 182a, 282, and 382. Alternatively, the adhesive may be applied to the top surface 10, 110, 110a, 210, and 310 or bottom surface 20, 120, 120a, 220, and 320, or both surfaces of the implant 1, 101, 101a, 201, and 301.

The foregoing describes various non-limiting examples of how the one or two integration plates 82, 182, 182a, 282, and 382 may be joined together with the implant 1, 101, 101a, 201, and 301.

Other Implant Features

The implant 1 may comprise some or all of the following implant features, for example. In some aspects, the interbody spinal implant 1 is substantially hollow and has a generally oval-shaped transverse cross-sectional area with smooth, rounded, or both smooth and rounded lateral sides 30 and posterior-lateral corners. The implant 1 includes at least one vertical aperture 60 that extends the entire height of the implant body 2. The vertical aperture 60 defines an interior surface 60a or hollow cavity within the implant 1, which may be filled with bone growth inducing materials. The vertical aperture (a) extends from the top surface to the bottom surface, (b) has a size and shape predetermined to maximize the surface area of the top surface and the bottom surface available proximate the anterior and posterior portions while maximizing both radiographic visualization and access to the substantially hollow center, and (c) optionally defines a transverse rim. The vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim.

As illustrated in FIG. 1 and FIG. 2A, the implant 1 has an opening 90 in the anterior portion 40. In one embodiment, the posterior portion 50 may have a similarly shaped opening 90 (not shown). In some aspects, only the anterior portion 40 has the opening 90 while the posterior portion 50 has an alternative opening 92 (which may have a size and shape different from the opening 90). The opening 92 defines an interior surface 92a or hollow cavity, which may be filled with bone growth inducing materials.

The opening 90, 290, and 390 has a number of functions. One function is to facilitate manipulation of the implant 1, 201, and 301 by the caretaker. Thus, the caretaker may insert a surgical tool into the opening 90, 290, and 390 and, through the engagement between the surgical tool and the opening 90, 290, and 390, manipulate the implant 1, 201, and 301. The opening 90, 290, and 390 may be threaded to enhance the engagement. A suitable surgical tool, such as a distractor (not shown), may be selected by one of ordinary skill in the art.

As best shown in FIG. 7 and FIG. 8, the anterior portion 140, 140a may have a tapered nose 142, 142a to facilitate insertion of the implant 101.

The implant 1 may further include at least one transverse aperture 70 that extends the entire transverse length of the implant body. The transverse aperture 70 defines an interior surface 70a or hollow cavity, which may be filled with bone growth inducing materials. The at least one transverse aperture 70 may provide improved visibility of the implant 1 during surgical procedures to ensure proper implant placement and seating, and may also improve post-operative assessment of implant fusion. The transverse aperture 70 may be broken into two, separate sections by an intermediate wall. Suitable shapes and dimensions for the transverse aperture 70 may be selected by one of ordinary skill in the art. In particular, all edges of the transverse aperture 70 may be rounded, smooth, or both. The intermediate wall may be made of the same material as the remainder of the body 2 of the implant 1 (e.g., plastic), or it may be made of another material (e.g., metal). The intermediate wall may offer one or more of several advantages, including reinforcement of the implant 1 and improved bone graft containment.

The implant 1 may be provided with a solid rear wall (not shown). The rear wall may extend the entire width of the implant body and nearly the entire height of the implant body. Thus, the rear wall can essentially close the anterior portion 40 of the implant 1. The rear wall may offer one or more of several advantages, including reinforcement of the implant 1 and improved bone graft containment. In the cervical application, it may be important to prevent bone graft material from entering the spinal canal.

The implant 1 may also have a lordotic angle to facilitate alignment. One lateral side 30 is preferably generally greater in height than the opposing lateral side 30. Therefore, the implant 1 may better compensate for the generally less supportive bone found in certain regions of the vertebral endplate. As much as seven degrees of lordosis (or more) may be built into the implant 1 to help restore cervical balance.

To enhance movement resistance and provide additional stability under spinal loads in the body, the implant 1, 101,

101a, 201, and 301 may comprise one or more anti-expulsion edges 8, 108, 108a, 208, and 308 that tend to "dig" into the end-plates slightly and help to resist expulsion. The anti-expulsion edges 8, 108, 108a, 208, and 308 may be present on the top surface 81 of the integration plate 82 affixed to the top surface 10, 110, 110a, 210, and 310; the bottom surface 20, 120, 120a, 220, and 320; or both surfaces of the implant 1, 101, 101a, 201, and 301. Alternatively, the anti-expulsion edges 8, 108, 108a, 208, and 308 may be present on the top surface 10, 110, 110a, 210, and 310; the bottom surface 20, 120, 120a, 220, and 320; or both surfaces of the body of the implant 1, 101, 101a, 201, and 301.

By way of example, FIG. 6 shows an anti-expulsion edge 8 on the top surface 81 of the integration plate 82 and the bottom surface 20 of the anterior face 40 of the implant 1. Each anti-expulsion edge 8 may protrude above the plane of the top surface 81 of the integration plate 82 and bottom surface 20, with the amount of protrusion increasing toward the anterior face 40 and the highest protrusion height P at the anterior-most edge of the top surface 81 of the integration plate 82 or bottom surface 20.

An anti-expulsion edge 8, 108, 108a, 208, and 308 may be oriented toward the anterior portion 40, 140, 140a, 240, and 340, or the posterior portion 50, 150, 150a, 250, and 350, or either of the opposing lateral sides 30, 130, 130a, 230, and 330. The orientation of the anti-expulsion edge 8, 108, 108a, 208, and 308 may depend on the intended orientation of the implant 1, 101, 101a, 201, and 301 when it has been implanted between vertebrae in the patient.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant 1 is to be seated near the center of the vertebral endplate or the implant 1 is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1 to accept and share stress transmitted from the endplates. In addition, spared endplates minimize the concern that BMP might erode the cancellous bone.

Interbody spinal implant 1 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, the surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1 may provide secure seating and prove difficult to remove. Thus, certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration.

Surgical implants and methods tension the vertebral annulus via distraction. These embodiments and methods may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants and the associated surgical technique have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact, and the sides of the implant 1, 101, 101a, 201, and 301 may have smooth surfaces to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a composite implant formed of top and optional bottom plates (components), for example, made out of titanium. The integration surfaces exposed to the vertebral body have a roughened surface topography 80 to allow for bony in-growth over time, and to provide resistance against expulsion. The top and bottom titanium plates may be assembled together with the implant body. The net result is a composite implant that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant is inserted in the prepared disc space via a procedure which does not destroy the end-plates, and if the implant contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. An interbody spinal implant comprising:
a body that is generally oval-shaped in transverse cross section, and comprises a top surface, a bottom surface, opposing lateral sides, opposing anterior and posterior portions, a sharp edge at the junction of the anterior portion and the top surface and at the junction of the anterior portion and the bottom surface, a substantially hollow center, and a single vertical aperture extending from the top surface to the bottom surface, having maximum width at its center, and defining a transverse rim on the top surface and on the bottom surface, said transverse rim having a posterior thickness greater than an anterior thickness, and having a blunt and radiused portion along the top of each lateral side and the top of the posterior portion, wherein the portion of the transverse rim that is not blunt and radiused has a roughened surface topography comprising macro features, micro features, and nano features, and wherein the blunt and radiused portion, the opposing lateral sides, and the opposing anterior and posterior portions do not include any roughened surface topography but do include a substantially smooth surface comprising nano features.

2. The interbody spinal implant of claim 1, wherein the single vertical aperture is surrounded by internal surfaces of the body comprising a first graft contact surface comprising micro features and nano features.

3. The interbody spinal implant of claim 2, wherein the substantially hollow center is surrounded by internal surfaces of the body comprising a second graft contact surface comprising micro features and nano features.

4. The interbody spinal implant of claim 3, wherein each of the micro features have a mean spacing between about 20 to 400 microns, a maximum peak-to-valley height between about 2 to 40 microns, and an average amplitude between about 1 to 20 microns, and each of the nano features have a mean spacing between about 0.5 to 20 microns, a maximum peak-to-valley height between about 0.2 to 2 microns, and an average amplitude between about 0.1 to 1 microns.

5. The interbody spinal implant of claim 3, wherein each of the micro features have a mean spacing between about 100 to 300 microns, a maximum peak-to-valley height between about 2 to 20 microns, and an average amplitude between about 4 to 10 microns, and each of the nano features have a mean spacing between about 1 to 15 microns, a maximum peak-to-valley height between about 0.2 to 1.8 microns, and an average amplitude between about 0.01 to 1 microns.

6. The interbody spinal implant of claim 3, wherein each of the micro features have a mean spacing between about 200 to 250 microns, a maximum peak-to-valley height between about 9 to 13 microns, and an average amplitude between about 2 to 6 microns; and each of the nano features have a mean spacing between about 5 to 12 microns, a maximum peak-to-valley height between about 0.3 to 1.3 microns, and an average amplitude between about 0.03 to 0.06 microns.

7. The interbody spinal implant of claim 1, wherein the roughened surface topography comprises a roughness average amplitude, Ra, of about 8 to 200 microns, and the substantially smooth surface comprises a roughness average amplitude, Ra, of about 0.01 to 2 microns.

8. The interbody spinal implant of claim 1, wherein the macro features have a mean spacing between about 400 to 2000 microns, a maximum peak-to-valley height between about 40 to 500 microns, and an average amplitude between about 20 to 200 microns; the micro features have a mean spacing between about 20 to 400 microns, a maximum peak-to-valley height between about 2 to 40 microns, and an average amplitude between about 1 to 20 microns; and each of the nano features have a mean spacing between about 0.5 to 20 microns, a maximum peak-to-valley height between about 0.2 to 2 microns, and an average amplitude between about 0.1 to 1 microns.

9. The interbody spinal implant of claim 1, wherein the body comprises titanium or a titanium alloy.

10. The interbody spinal implant of claim 1, wherein the macro features have a mean spacing between about 750 to 1750 microns, a maximum peak-to-valley height between about 150 to 400 microns, and an average amplitude between about 50 to 150 microns; the micro features have a mean spacing between about 100 to 300 microns, a maximum peak-to-valley height between about 2 to 20 microns, and an average amplitude between about 4 to 10 microns; and each of the nano features have a mean spacing between about 1 to 15 microns, a maximum peak-to-valley height between about 0.2 to 1.8 microns, and an average amplitude between about 0.01 to 1 microns.

11. The interbody spinal implant of claim 1, wherein the macro features have a mean spacing between about 1000 to 1500 microns, a maximum peak-to-valley height between about 250 to 300 microns, and an average amplitude between about 100 to 125 microns; the micro features have a mean spacing between about 200 to 250 microns, a maximum peak-to-valley height between about 9 to 13 microns, and an average amplitude between about 2 to 6 microns; and each of the nano features have a mean spacing between about 5 to 12 microns, a maximum peak-to-valley height between about 0.3 to 1.3 microns, and an average amplitude between about 0.03 to 0.06 microns.

12. An interbody spinal implant, comprising a body that is generally oval-shaped in transverse cross section, and comprises a top surface, a bottom surface, opposing lateral sides, opposing anterior and posterior portions, a substantially hollow center, and a single vertical aperture extending from the top surface to the bottom surface and having maximum width at its center, wherein a portion of the top surface and a portion of the bottom surface is recessed, wherein the non-recessed portion of the top surface and the non-recessed portion of the bottom surface comprises a blunt and radiused portion, and wherein the blunt and radiused portion, the opposing lateral sides, and the opposing anterior and posterior portions do not include any roughened surface topography but do include a substantially smooth surface comprising nano features; and, a first integration plate inserted into the recessed portion of the top surface, and a second integration plate inserted into the recessed portion of the bottom surface, each of the first integration plate and the second integration plate having a top, a bottom, an anterior side, a posterior side, and a single vertical aperture extending from the top to the bottom, aligning with the single vertical aperture of the body, and defining a transverse rim with a varying width and having a posterior thickness greater than an anterior thickness and a roughened surface topography comprising macro features, micro features, and nano features, wherein each of the first integration plate and the second integration plate comprise a sharp edge at anterior side of the top.

13. The interbody spinal implant of claim 12, wherein the single vertical aperture is surrounded by internal surfaces of the body comprising a first graft contact surface comprising micro features and nano features.

14. The interbody spinal implant of claim 13, wherein the substantially hollow center is surrounded by internal surfaces of the body comprising a second graft contact surface comprising micro features and nano features.

15. The interbody spinal implant of claim 14, wherein each of the micro features have a mean spacing between about 20 to 400 microns, a maximum peak-to-valley height between about 2 to 40 microns, and an average amplitude between about 1 to 20 microns, and each of the nano features have a mean spacing between about 0.5 to 20 microns, a maximum peak-to-valley height between about 0.2 to 2 microns, and an average amplitude between about 0.1 to 1 microns.

16. The interbody spinal implant of claim 14, wherein each of the micro features have a mean spacing between about 100 to 300 microns, a maximum peak-to-valley height between about 2 to 20 microns, and an average amplitude between about 4 to 10 microns, and each of the nano features have a mean spacing between about 1 to 15 microns, a maximum peak-to-valley height between about 0.2 to 1.8 microns, and an average amplitude between about 0.01 to 1 microns.

17. The interbody spinal implant of claim 14, wherein each of the micro features have a mean spacing between about 200 to 250 microns, a maximum peak-to-valley height between about 9 to 13 microns, and an average amplitude between about 2 to 6 microns; and each of the nano features have a mean spacing between about 5 to 12 microns, a maximum peak-to-valley height between about 0.3 to 1.3 microns, and an average amplitude between about 0.03 to 0.06 microns.

18. The interbody spinal implant of claim 12 wherein the roughened surface topography comprises a roughness average amplitude, Ra, of about 8 to 200 microns, and the substantially smooth surface comprises a roughness average amplitude, Ra, of about 0.01 to 2 microns.

19. The interbody spinal implant of claim 12, wherein the macro features have a mean spacing between about 400 to 2000 microns, a maximum peak-to-valley height between about 40 to 500 microns, and an average amplitude between about 20 to 200 microns, the micro features have a mean spacing between about 20 to 400 microns, a maximum peak-to-valley height between about 2 to 40 microns, and an average amplitude between about 1 to 20 microns, and each of the nano features have a mean spacing between about 0.5 to 20 microns, a maximum peak-to-valley height between about 0.2 to 2 microns, and an average amplitude between about 0.01 to 1 microns.

20. The interbody spinal implant of claim 12, wherein the macro features have a mean spacing between about 750 to 1750 microns, a maximum peak-to-valley height between about 150 to 400 microns, and an average amplitude between about 50 to 150 microns; the micro features have a mean spacing between about 100 to 300 microns, a maximum peak-to-valley height between about 2 to 20 microns, and an average amplitude between about 4 to 10 microns; and each of the nano features have a mean spacing between about 1 to 15 microns, a maximum peak-to-valley height between about 0.2 to 1.8 microns, and an average amplitude between about 0.01 to 1 microns.

21. The interbody spinal implant of claim 12, wherein the macro features have a mean spacing between about 1000 to 1500 microns, a maximum peak-to-valley height between about 250 to 300 microns, and an average amplitude between about 100 to 125 microns; the micro features have a mean spacing between about 200 to 250 microns, a maximum peak-to-valley height between about 9 to 13 microns, and an average amplitude between about 2 to 6 microns; and each of the nano features have a mean spacing between about 5 to 12 microns, a maximum peak-to-valley height between about 0.3 to 1.3 microns, and an average amplitude between about 0.03 to 0.06 microns.

22. The interbody spinal implant of claim 12, wherein the body comprises titanium or a titanium alloy.

* * * * *